(12) United States Patent
Nallur

(10) Patent No.: US 6,692,915 B1
(45) Date of Patent: Feb. 17, 2004

(54) SEQUENCING A POLYNUCLEOTIDE ON A GENERIC CHIP

(76) Inventor: Girish N. Nallur, 1 Marilyns La., Guilford, CT (US) 06437

( * ) Notice: Subject to any disclaimer, the term of this patent is extended or adjusted under 35 U.S.C. 154(b) by 0 days.

(21) Appl. No.: 09/619,812

(22) Filed: Jul. 20, 2000

Related U.S. Application Data

(60) Provisional application No. 60/145,043, filed on Jul. 22, 1999.

(51) Int. Cl.[7] .................... C12Q 1/68; C12P 19/34; C12N 13/00; G01N 33/566; G01N 33/564; G01N 33/537; G01N 33/48; G01N 33/50
(52) U.S. Cl. .............. 435/6; 435/91.1; 435/173.1; 435/320.1; 436/501; 436/508; 436/538; 436/815; 702/19; 702/20
(58) Field of Search .............. 435/6, 91, 172.3, 435/320.1, 805; 702/19, 20; 436/501, 508, 538

(56) References Cited

U.S. PATENT DOCUMENTS

| | | | | |
|---|---|---|---|---|
| 4,988,617 A | | 1/1991 | Landegren et al. | 435/6 |
| 5,002,867 A | | 3/1991 | Macevicz | 435/6 |
| 5,215,899 A | * | 6/1993 | Dattagupta | 435/6 |
| 5,445,934 A | | 8/1995 | Fodor et al. | 435/6 |
| 5,503,980 A | | 4/1996 | Cantor | 435/6 |
| 5,508,169 A | | 4/1996 | Deugau et al. | 435/6 |
| 5,552,270 A | | 9/1996 | Khrapko et al. | 435/6 |
| 5,599,672 A | | 2/1997 | Liang et al. | 435/6 |
| 5,631,134 A | | 5/1997 | Cantor | 435/6 |
| 5,700,637 A | | 12/1997 | Southern | 435/6 |
| 5,714,320 A | | 2/1998 | Kool | 435/6 |
| 5,866,305 A | | 2/1999 | Chon et al. | 435/6 |
| 5,925,525 A | | 7/1999 | Fodor et al. | 435/6 |
| 5,952,174 A | | 9/1999 | Nikiforov et al. | 435/6 |
| 6,013,445 A | | 1/2000 | Albrecht et al. | 435/6 |
| 6,025,139 A | | 2/2000 | Yager et al. | 435/6 |
| 6,027,889 A | | 2/2000 | Barany et al. | 435/6 |
| 6,037,130 A | * | 3/2000 | Tyagi et al. | 435/6 |
| 6,277,607 B1 | * | 8/2001 | Tyagi et al. | 435/91.2 |

FOREIGN PATENT DOCUMENTS

| | | | | |
|---|---|---|---|---|
| EP | 0373203 | | 8/1994 | C12Q/1/68 |
| WO | WO 89/10977 | | 11/1989 | C12Q/1/68 |
| WO | WO 99/28505 | | 6/1999 | C12Q/1/68 |
| WO | WO-99/28505 A1 | * | 6/1999 | C12Q/1/68 |

OTHER PUBLICATIONS

Velculescu et al., Science, vol. 270, pp. 484–487, Oct. 20, 1995.*
Higgins et al. DNA–Joining Enzymes: A Review, Methods in Enzymes, vol. 68, pp. 54–56, (1979).
Engler et al., The Enzymes, vol. 15, pp. 16–17 (1982).

* cited by examiner

Primary Examiner—John S. Brusca
Assistant Examiner—Shubo "Joe" Zhou
(74) Attorney, Agent, or Firm—Bromberg, Sunstein LLP

(57) ABSTRACT

The present invention describes methods and devices for sequencing a polynucleotide by determining subsets of composite subsequences present in nucleic acid subsamples generated from the sample polynucleotide. A hairpin primer interrogates the composite subsequences in a two-step process resulting first in a polymerase extended product whose synthesis identifies the first subsequence of the composite subsequence. The second subsequences are identified by hybridizing the polymerase extended products or amplified products therefrom to an array of capture probes wherein each capture probe is positionally distinguishable from other capture probes. The invention is applicable to the quantitative determination of the presence of nucleic acids in a sample, for identifying differences in the relative abundance of nucleic acids in a mixture of nucleic acids, and generally, to diagnostic aids for the identification of nucleic acids.

16 Claims, 7 Drawing Sheets

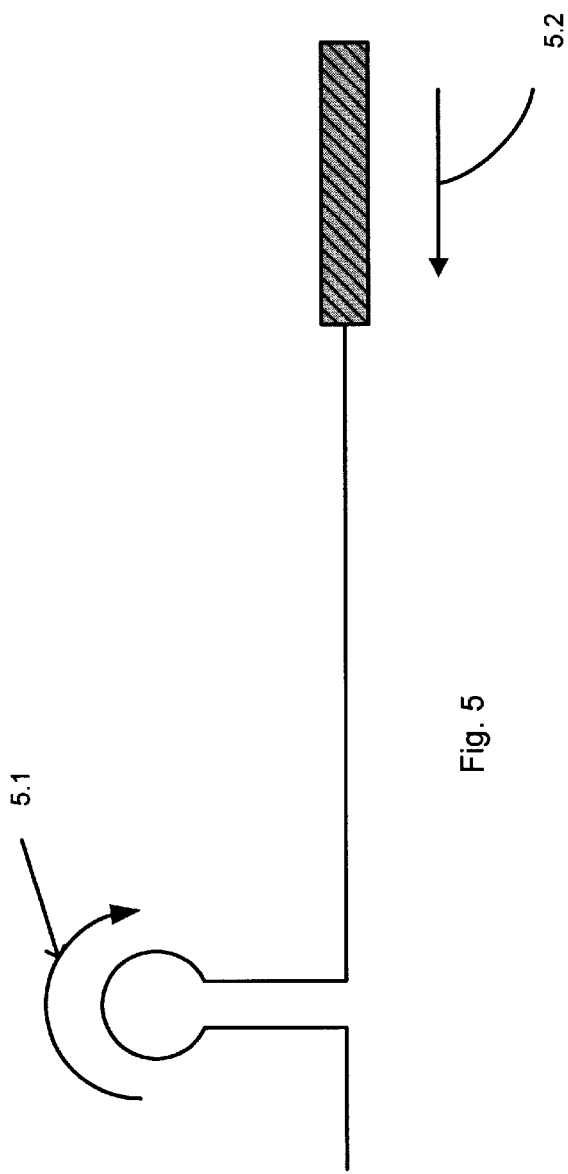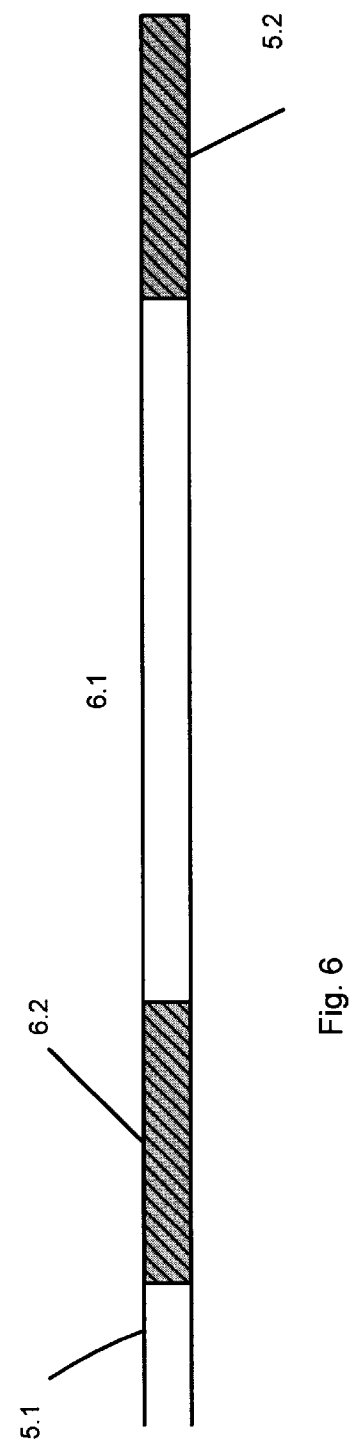

Type II Cleavage Product

SEQUENCE LISTING

<160> NUMBER OF SEQ ID NOS: 11

<210> SEQ ID NO 1
<211> LENGTH: 26
<212> TYPE: DNA
<213> ORGANISM: Artificial Sequence

```
<220> FEATURE:
<223> OTHER INFORMATION: linker oligonucleotide for pBlue Sfi AB plus
      strand

<400> SEQUENCE: 1
aattgtaata cgactcacta tagggc                                          26

<210> SEQ ID NO 2
<211> LENGTH: 26
<212> TYPE: DNA
<213> ORGANISM: Artificial Sequence
<220> FEATURE:
<223> OTHER INFORMATION: adapter oligonucleotide for pBlue Sfi minus
      strand

<400> SEQUENCE: 2
aagcgcccta tagtgagtcg tattac                                          26

<210> SEQ ID NO 3
<211> LENGTH: 20
<212> TYPE: DNA
<213> ORGANISM: Homo sapiens
<220> FEATURE:
<223> OTHER INFORMATION: anchoring oligonucleotide
      human p53 gene plus strand

<400> SEQUENCE: 3
ctcaaagagg ccaaggcagg                                                 20

<210> SEQ ID NO 4
<211> LENGTH: 37
<212> TYPE: DNA
<213> ORGANISM: Artificial Sequence
<220> FEATURE:
<223> OTHER INFORMATION: Primer for extension

<400> SEQUENCE: 4
cagatcgtcg ttcactactg cacggatgca cgcacct                              37

<210> SEQ ID NO 5
<211> LENGTH: 20
<212> TYPE: DNA
<213> ORGANISM: Artificial Sequence
<220> FEATURE:
<223> OTHER INFORMATION: PCR primer

<400> SEQUENCE: 5
cactactgca cggatgcacg                                                 20

<210> SEQ ID NO 6
<211> LENGTH: 20
<212> TYPE: DNA
<213> ORGANISM: Artificial Sequence
<220> FEATURE:
<223> OTHER INFORMATION: positioning oligonucleotide

<400> SEQUENCE: 6
cgacgatctg aggtgcgtgc                                                 20

<210> SEQ ID NO 7
<211> LENGTH: 25
<212> TYPE: DNA
<213> ORGANISM: Artificial Sequence
<220> FEATURE:
<223> OTHER INFORMATION: primer for rolling circle amplification

<400> SEQUENCE: 7
```

```
aagctgcatc cgtgcagtag tgaac                                              25

<210> SEQ ID NO 8
<211> LENGTH: 20
<212> TYPE: DNA
<213> ORGANISM: Artificial Sequence
<220> FEATURE:
<223> OTHER INFORMATION: capture probe

<400> SEQUENCE: 8
cgtgcatccg tgcagtcgtg                                                    20

<210> SEQ ID NO 9
<211> LENGTH: 20
<212> TYPE: DNA
<213> ORGANISM: Artificial Sequence
<220> FEATURE:
<223> OTHER INFORMATION: capture probe

<400> SEQUENCE: 9
cactactgca cggatgcacg                                                    20

<210> SEQ ID NO 10
<211> LENGTH: 24
<212> TYPE: DNA
<213> ORGANISM: Artificial Sequence
<220> FEATURE:
<223> OTHER INFORMATION: capture probe

<400> SEQUENCE: 10
aaaacgtgca tccgtgcagt cgtg                                               24

<210> SEQ ID NO 11
<211> LENGTH: 20
<212> TYPE: DNA
<213> ORGANISM: Homo sapiens
<220> FEATURE:
<223> OTHER INFORMATION: chromosome 8, clone RP11-709L14

<400> SEQUENCE: 11
gagcccagga gttcaagacc                                                    20
```

SEQUENCING A POLYNUCLEOTIDE ON A GENERIC CHIP

CROSS REFERENCE TO RELATED APPLICATIONS

This application claims benefit from Provisional Application Serial No. 60/145,043 filed Jul. 22, 1999.

FIELD OF THE INVENTION

The invention relates to a method of analyzing a polynucleotide sequence. This invention is also directed to diagnostic aids for analyzing the nucleic acid composition and content of biological samples, including samples derived from medical and agricultural sources.

BACKGROUND OF THE INVENTION

The genomics revolution has spurned a significant interest in the creation of personalized drugs based on the genetic constitution, or 'genotype' of the recipient and in related scientific research areas such as high throughput drug discovery, diagnostics in human subjects, animal health and cloning, and the genetic selection of plants with desired traits. Consequently, robust technology platforms have been created for the rapid identification of genomics sequence and the creation of sequence databases wherefrom making electronic comparisons can identify even small differences in sequences between individuals (such as, single nucleotide polymorphisms, or SNPs). It is estimated that the ~80,000 human genes contain about 200,000 cSNPs, (i.e., SNPs that lie in coding regions) whereas over several million randomly chosen SNPs are likely to be detected in the genome.

It has been suggested that testing a dense panel of SNPs arrayed across both coding and noncoding regions, termed 'ancestral haplotypes', in affected individuals and in controls may be an appropriate strategy to identify associations that narrowly locate the neighborhood of a susceptibility or resistance gene. A dense map of SNPs with at least 100,000 SNPs is estimated to satisfy the resolution required.

Recent novel approaches to assessing DNA sequence differences between individuals, such as, minisequencing, multiplex reverse dot blots, DNA microarrays, and the TaqMan approach have lent a significant impetus to the speed, cost efficiency and accuracy of association studies.

Other strategies described in the art for identification of polymorphisms have included a genome simplification or complexity reduction step, including construction of shotgun libraries in BACs, PACs, or cosmids using DNA samples from a limited number of subjects. Clones from the library are sequenced. Alternatively, hybridization or enzymatic approaches (such as RDA or mismatch scanning using bacterial proteins or enzymes involved in homologous recombination) have been used. These latter approaches are rapid and cost effective and eliminate the need for sequencing extensive regions of genomic DNA for identifying polymorphisms.

Yet, the above methods suffer from 2 major disadvantages, a) lack of throughput, and b) inadequate representation of the genome per iteration. As such, there is a need for further improvements in the technology for high throughput genomics analytical methods, in particular, detection of SNPs.

SUMMARY OF THE INVENTION

This invention features methods for sensitively detecting the presence of a nucleic acid in a sample. Described herein are methods for synergistic multiplexed amplifications of nucleic acids. Multiple individual chemical and biochemical reactions for target identification, amplification and partitioning and detection of each signal independently of other similar signals in the multiplexed reaction can be caused to occur simultaneously.

Consequently, it is an object of this invention to provide a method for identifying nucleic acids in a sample.

It is an object of this invention to quantify nucleic acids from a sample.

It is an object of this invention to rapidly and cost-effectively determine the quantitative presence of nucleic acids in a sample.

It is an object of this invention to provide methods for the multiplexed analysis of nucleic acids from a sample.

It is an object of this invention to identify qualitative differences between nucleic acids of two or more organisms of the same species.

It is an object of this invention to provide a method for comparing the amount of nucleic acids present in two or more samples.

It is an object of this invention to identify an organism by identifying presence of the genomic nucleic acids of the organism in a sample.

It is an object of this invention to quantify the presence of nucleic acids of an organism relative to the amount of nucleic acids of another organism present in the same sample.

It is an object of this invention to identify the physiological state of an organism by quantifying gene expression in the sample.

In one aspect, the invention features a method of analyzing a polynucleotide, e.g., detecting a genetic event, e.g., a single nucleotide polymorphism, in a sample.

The method includes:

1. providing a sample which includes a sample polynucleotide sequence to be analyzed, said sample polynucleotide being at least partially single stranded and containing a region of recognizable sequence adjacent to the single stranded terminus;
2. (a) annealing an effective amount of sample sequence to a hairpin primer, wherein the hairpin primer comprises at least one copy of a nucleotide sequence complementary to the sequence of the sample polynucleotide sequence and optionally,
    (b) extending the hairpin primer with an effective amount of at least two types of nucleotide triphosphates and an effective amount of a polymerase enzyme to yield a product, e.g., a single stranded polymerase extended product complementary to a substantial portion of the single stranded region of the sample polynucleotide; and
    (c) optionally, amplifying the polymerase extended product to produce amplified products, herein termed amplified products;
3. analyzing said product from 2 (a, b or c) by providing an array of a plurality of capture probes, wherein each of the capture probes is positionally distinguishable from other capture probes of the plurality on the array, and wherein each positionally distinguishable capture probe includes at least one unique (i.e., not repeated in another capture probe) region, optionally, adjacent to a common (repeated in all the capture probes) region; hybridizing the amplified products with the array of capture probes, thereby analyzing the sample sequence.

In preferred embodiments, analyzing a sample polynucleotide includes, e.g., sequencing the polynucleotide sequence, e.g., by sequencing by hybridization or positional sequencing by hybridization, detecting the presence of, or identifying a genetic event, e.g., a SNP, in a target nucleic acid, e.g., a DNA.

In preferred embodiments, the genetic event is within 12 bases, more preferably within 1, 2, 3, 4, 5, or 6 bases in the single stranded portion of sample polynucleotide that is adjacent to and abuts the double stranded region; more specifically, in the region of the single stranded portion of the sample polynucleotide farthest from the single stranded terminus, or is sufficiently close to the double strand portion of the sample polynucleotide that a mismatch would inhibit DNA polymerase-based extension from the sample polynucleotide/hairpin primer complex.

In preferred embodiments, the genetic event is located anywhere within the single stranded portion of the sample polynucleotide.

In preferred embodiments, the target polynucleotide in the sample is amplified, e.g., by PCR, prior to contact with a hairpin primer.

In preferred embodiments, the hairpin primer includes a site for a type 2s restriction enzyme and the site is positioned, e.g., such that a type 2s restriction enzyme binding at the site cleaves adjacent the region which binds the sample sequence or cleaves in the region which binds the sample sequence.

In a preferred embodiment, a region of the hairpin primer is complementary to a genetic event, e.g., a mutation or SNP, and hybridizes effectually to sample nucleic acid having the event and sample nucleic acid not having the event.

In preferred embodiments the polynucleotide sequence is: a DNA molecule: all or part of a known gene; wild type DNA; mutant DNA; a genomic fragment, particularly a human genomic fragment; a cDNA, particularly a human cDNA.

In preferred embodiments the polynucleotide sequence is: an RNA molecule: nucleic acids derived from RNA transcripts; wild type RNA; mutant RNA, particularly a human RNA.

In preferred embodiments the polynucleotide sequence is: a human sequence; a non-human sequence, e.g., a mouse, rat, pig, primate.

In preferred embodiments the method is performed: on a sample from a human subject; and a sample from a prenatal subject, as part of genetic counseling; to determine if the individual from whom the target nucleic acid is taken should receive a drug or other treatment; to diagnose an individual for a disorder or for predisposition to a disorder; to stage a disease or disorder.

In preferred embodiments the capture probes are single stranded probes in an array.

In preferred embodiments the capture probes have a structure comprising a double stranded portion and a single stranded portion in an array.

In preferred embodiments hybridization to the array is detected by mass spectrophotometry, e.g., by MALDI-TOF mass spectrophotometry.

In a preferred embodiment the amplified product, which hybridizes to a capture probe, or the capture probe, is the substrate of or template for an enzyme mediated reaction.

For example, after hybridization to the capture probe, the amplified product is ligated to the capture probe, or after the hybridization it is extended along the capture probe.

In preferred embodiments the method includes one or more enzyme mediated reactions in which a nucleic acid used in the method, e.g., an amplified product, a capture probe, a sequence to be analyzed, or a molecule which hybridizes thereto, is a substrate or template for the enzyme mediated reaction. The enzyme mediated reaction can be: an extension reaction, e.g., a reaction catalyzed by a polymerase; a linking reaction, e.g., a ligation, e.g., a reaction catalyzed by a ligase; or a nucleic acid cleavage reaction, e.g., a cleavage catalyzed by a restriction enzyme, e.g., a Type IIs enzyme or an exonuclease. The amplified product, which hybridizes with the capture probe, can be the substrate in an enzyme mediated reaction, e.g., it can be ligated to a strand of the capture probe. Alternatively, the capture probe can be extended along the hybridized amplified products. (Any of the extension reactors discussed herein can be performed with labeled, or chain terminating, subunits). The capture probe duplex can be the substrate for a cleavage reaction. These reactions can be used to increase the specificity of the method or to otherwise aid in detection, e.g., by providing a signal.

Methods of U.S. Pat. No. 5,503,980 and U.S. Pat. No. 5,631,134, both of which are hereby incorporated by reference can be used herein, particularly, the array and array-related steps recited herein can use methods taught in these patents.

In preferred embodiments, the method includes providing an array having a plurality of capture probes, wherein each of the capture probes is a) positionally distinguishable from the other capture probes of the plurality and has a unique variable region (not repeated in another capture probe of the plurality), b) has a variable region capable of hybridizing adjacent to the genetic event; and has a 3' end capable of serving as a priming site for extension; hybridizing the amplified products having a genetic event to a capture probe of the array, (preferably the region of the amplified products having a genetic event hybridizes adjacent to the variable region of a capture probe); and using the 3' end of the capture probe to extend across the region of genomic nucleic acid having a genetic event with one or more terminating base species, where if more than one is used each has a unique distinguishable label, e.g., label 1 for base A, label 2 for base T, label 3 for base G, and label 4 for base C; thereby analyzing the amplified products.

In a preferred embodiment, at least one reaction step is performed on a three- dimensional array, e.g., a gel array.

Preferably, a hairpin primer has about 15–1500 nucleotides, and more preferably about 24–500 nucleotides and most preferably about 30–150 nucleotides.

The hairpin primer is constructed of DNA or RNA or analogs thereof. Preferably, the hairpin primer is constructed of DNA.

The polymerase enzyme can be any that affects the synthesis of the polymerase extended product.

In another aspect, the invention features a method of analyzing a polynucleotide, e.g., detecting a genetic event, e.g., a single nucleotide polymorphism, in a sample.

The method includes:
1. providing a sample which includes a sample polynucleotide sequence to be analyzed, said sample polynucleotide being at least partially single stranded and containing a region of recognizable sequence adjacent to the single stranded terminus;
2. (a) annealing an effective amount of sample sequence to a hairpin primer, wherein the hairpin primer comprises at least one copy of a nucleotide sequence complementary to the sequence of the sample polynucleotide sequence and optionally,
   (b) extending the hairpin primer with an effective amount of at least two types of nucleotide triphosphates and an effective amount of a polymerase enzyme to yield a product, e.g., a single stranded polymerase extended product complementary to a substantial portion of the single stranded region of the sample polynucleotide; and (c) optionally, amplifying the polymerase extended product to produce amplified products, herein termed amplified products;

3. analyzing said product from 2 (b) or (c) by providing a separation means, e.g., a gel for electrophoretic separation of nucleic acid fragments, e.g., polyacrylamide gel, agarose gel, capillary electrophoresis or other described in the art.

In preferred embodiments, analyzing a sample polynucleotide includes, e.g., sequencing the polynucleotide sequence, e.g., by sequencing by hybridization or positional sequencing by hybridization, detecting the presence of, or identifying a genetic event, e.g., a SNP, in a target nucleic acid, e.g., a DNA.

In preferred embodiments, the genetic event is within 12 bases, more preferably within 1, 2, 3, 4, 5, or 6 bases in the single stranded portion of sample polynucleotide that is adjacent to and immediately follows the double stranded region; more specifically, in the region of the single stranded portion of the sample polynucleotide farthest from the single stranded terminus, or is sufficiently close to the double strand portion of the sample polynucleotide that a mismatch would inhibit DNA polymerase-based extension from the sample polynucleotide/hairpin primer complex.

In equally preferred embodiments, the genetic event is located anywhere within the single stranded portion of the sample polynucleotide.

In preferred embodiments, the target polynucleotide in the sample is amplified, e.g., by PCR, prior to contact with a hairpin primer.

In preferred embodiments, the hairpin primer includes a site for a type 2s restriction enzyme and the site is positioned, e.g., such that a type 2s restriction enzyme binding at the site cleaves adjacent the region which binds the sample sequence or cleaves in the region which binds the sample sequence.

In a preferred embodiment, a region of the hairpin primer is complementary to a genetic event, e.g., a mutation or SNP, and hybridizes effectually to sample nucleic acid having the event and sample nucleic acid not having the event.

In preferred embodiments the polynucleotide sequence is: a DNA molecule: all or part of a known gene; wild type DNA; mutant DNA; a genomic fragment, particularly a human genomic fragment; a cDNA, particularly a human cDNA.

In preferred embodiments the polynucleotide sequence is: an RNA molecule: nucleic acids derived from RNA transcripts; wild type RNA; mutant RNA, particularly a human RNA.

In preferred embodiments the polynucleotide sequence is: a human sequence; a non-human sequence, e.g., a mouse, rat, pig, primate.

In preferred embodiments the method is performed: on a sample from a human subject; and a sample from a prenatal subject, as part of genetic counseling; to determine if the individual from whom the target nucleic acid is taken should receive a drug or other treatment; to diagnose an individual for a disorder or for predisposition to a disorder; to stage a disease or disorder.

In preferred embodiments the capture probes are single stranded probes in an array.

In preferred embodiments the capture probes have a structure comprising a double stranded portion and a single stranded portion in an array.

In preferred embodiments hybridization to the array is detected by mass spectrophotometry, e.g., by MALDI-TOF mass spectrophotometry.

In a preferred embodiment the amplified products (amplified products) which hybridizes to a capture probe, or the capture probe, is the substrate of or template for an enzyme mediated reaction.

For example, after hybridization to the capture probe, the amplified products is ligated to the capture probe, or after the hybridization it is extended along the capture probe.

In preferred embodiments the method includes one or more enzyme mediated reactions in which a nucleic acid used in the method, e.g., an amplified products, a capture probe, a sequence to be analyzed, or a molecule which hybridizes thereto, is a substrate or template for the enzyme mediated reaction. The enzyme mediated reaction can be: an extension reaction, e.g., a reaction catalyzed by a polymerase; a linking reaction, e.g., a ligation, e.g., a reaction catalyzed by a ligase; or a nucleic acid cleavage reaction, e.g., a cleavage catalyzed by a restriction enzyme, e.g., a Type IIs enzyme or an exonuclease. The amplified products which hybridizes with the capture probe can be the substrate in an enzyme mediated reaction, e.g., it can be ligated to a strand of the capture probe. Alternatively, the capture probe can be extended along the hybridized amplified products. (Any of the extension reactors discussed herein can be performed with labeled, or chain terminating, subunits). The capture probe duplex can be the substrate for a cleavage reaction. These reactions can be used to increase the specificity of the method or to otherwise aid in detection, e.g., by providing a signal.

Methods of U.S. Pat. No. 5,503,980 and U.S. Pat. No. 5,631,134, both of which are hereby incorporated by reference can be used herein, particularly, the array and array-related steps recited herein can use methods taught in these patents.

In preferred embodiments, the method includes providing an array having a plurality of capture probes, wherein each of the capture probes is a) positionally distinguishable from the other capture probes of the plurality and has a unique variable region (not repeated in another capture probe of the plurality), b) has a variable region capable of hybridizing adjacent to the genetic event; and has a 3' end capable of serving as a priming site for extension; hybridizing the amplified products having a genetic event to a capture probe of the array, (preferably the region of the amplified products having a genetic event hybridizes adjacent to the variable region of a capture probe); and using the 3' end of the capture probe to extend across the region of genomic nucleic acid having a genetic event with one or more terminating base species, where if more than one is used each has a unique distinguishable label, e.g., label 1 for base A, label 2 for base T, label 3 for base G, and label 4 for base C; thereby analyzing the amplified products.

In a preferred embodiment, at least one reaction step is performed on a three-dimensional array, e.g., a gel array.

Preferably, a hairpin primer has about 15–1500 nucleotides, and more preferably about 24–500 nucleotides and most preferably about 30–150 nucleotides.

The hairpin primer is constructed of DNA or RNA or analogs thereof. Preferably, the hairpin primer is constructed of DNA.

The polymerase enzyme can be any that affects the synthesis of the polymerase extended product.

In another aspect, the invention features a method of analyzing a polynucleotide, e.g., detecting a genetic event, e.g., a single nucleotide polymorphism, in a sample.

The method includes:
1. providing a sample which includes a sample polynucleotide sequence to be analyzed, said sample polynucleotide being at least partially single stranded and containing a region of recognizable sequence adjacent to the single stranded terminus;
2. (a) annealing an effective amount of sample sequence to a hairpin primer, wherein the hairpin primer comprises at least one copy of a nucleotide sequence complementary to the sequence of the sample polynucleotide sequence and optionally,
    (b) extending the hairpin primer with an effective amount of at least two types of nucleotide triphosphates and an effective amount of a polymerase enzyme to yield a product, e.g., a single stranded polymerase extended product complementary to a substantial portion of the single stranded region of the sample polynucleotide; and
    (c) optionally, amplifying the polymerase extended product to produce amplified products, herein termed amplified products;
    (d) cleaving the amplified products with a restriction enzyme, e.g., a type IIs restriction enzyme;
3. analyzing said cleaved product from 3 by providing an array of a plurality of capture probes, wherein each of the capture probes is positionally distinguishable from other capture probes of the plurality on the array, and wherein each positionally distinguishable capture probe includes at least one unique (i.e., not repeated in another capture probe) region, optionally, adjacent to a common (repeated in all the capture probes) region; hybridizing the amplified products with the array of capture probes, thereby analyzing the sample sequence.

In preferred embodiments, analyzing a sample polynucleotide includes, e.g., sequencing the polynucleotide sequence, e.g., by sequencing by hybridization or positional sequencing by hybridization, detecting the presence of, or identifying a genetic event, e.g., a SNP, in a target nucleic acid, e.g., a DNA.

In preferred embodiments, the genetic event is within 12 bases, more preferably within 1, 2, 3, 4, 5, or 6 bases in the single stranded portion of sample polynucleotide that is adjacent to and immediately follows the double stranded region; more specifically, in the region of the single stranded portion of the sample polynucleotide farthest from the single stranded terminus, or is sufficiently close to the double strand portion of the sample polynucleotide that a mismatch would inhibit DNA polymerase-based extension from the sample polynucleotide/hairpin primer complex.

In equally preferred embodiments, the genetic event is located anywhere within the single stranded portion of the sample polynucleotide.

In preferred embodiments, the target polynucleotide in the sample is amplified, e.g., by PCR, prior to contact with a hairpin primer.

In preferred embodiments, the hairpin primer includes a site for a type 2s restriction enzyme and the site is positioned, e.g., such that a type 2s restriction enzyme binding at the site cleaves adjacent the region which binds the sample sequence or cleaves in the region which binds the sample sequence.

In a preferred embodiment, a region of the hairpin primer is complementary to a genetic event, e.g., a mutation or SNP, and hybridizes effectually to sample nucleic acid having the event and sample nucleic acid not having the event.

In preferred embodiments the polynucleotide sequence is: a DNA molecule: all or part of a known gene; wild type DNA; mutant DNA; a genomic fragment, particularly a human genomic fragment; a cDNA, particularly a human cDNA.

In preferred embodiments the polynucleotide sequence is: an RNA molecule: nucleic acids derived from RNA transcripts; wild type RNA; mutant RNA, particularly a human RNA.

In preferred embodiments the polynucleotide sequence is: a human sequence; a non-human sequence, e.g., a mouse, rat, pig, primate.

In preferred embodiments the method is performed: on a sample from a human subject; and a sample from a prenatal subject, as part of genetic counseling; to determine if the individual from whom the target nucleic acid is taken should receive a drug or other treatment; to diagnose an individual for a disorder or for predisposition to a disorder; to stage a disease or disorder.

In preferred embodiments the capture probes are single stranded probes in an array.

In preferred embodiments the capture probes have a structure comprising a double stranded portion and a single stranded portion in an array.

In preferred embodiments hybridization to the array is detected by mass spectrophotometry, e.g., by MALDI-TOF mass spectrophotometry.

In a preferred embodiment the amplified sample that hybridizes to a capture probe, or the capture probe, is the substrate of or template for an enzyme mediated reaction.

For example, after hybridization to the capture probe, the amplified products is ligated to the capture probe, or after the hybridization it is extended along the capture probe.

In preferred embodiments the method includes one or more enzyme mediated reactions in which a nucleic acid used in the method, e.g., an amplified products, a capture probe, a sequence to be analyzed, or a molecule which hybridizes thereto, is a substrate or template for the enzyme mediated reaction. The enzyme mediated reaction can be: an extension reaction, e.g., a reaction catalyzed by a polymerase; a linking reaction, e.g., a ligation, e.g., a reaction catalyzed by a ligase; or a nucleic acid cleavage reaction, e.g., a cleavage catalyzed by a restriction enzyme, e.g., a Type IIs enzyme or an exonuclease. The amplified products that hybridizes with the capture probe can be the substrate in an enzyme-mediated reaction, e.g., it can be ligated to a strand of the capture probe. Alternatively, the capture probe can be extended along the hybridized amplified products. (Any of the extension reactors discussed herein can be performed with labeled, or chain terminating, subunits). The capture probe duplex can be the substrate for a cleavage reaction. These reactions can be used to increase the specificity of the method or to otherwise aid in detection, e.g., by providing a signal.

Methods of U.S. Pat. No. 5,503,980 and U.S. Pat. No. 5,631,134, both of which are hereby incorporated by reference can be used herein, particularly, the array and array-related steps recited herein can use methods taught in these patents.

In preferred embodiments, the method includes providing an array having a plurality of capture probes, wherein each of the capture probes is a) positionally distinguishable from the other capture probes of the plurality and has a unique variable region (not repeated in another capture probe of the plurality), b) has a variable region capable of hybridizing adjacent to the genetic event; and has a 3' end capable of serving as a priming site for extension; hybridizing the amplified products having a genetic event to a capture probe of the array, (preferably the region of the amplified products having a genetic event hybridizes adjacent to the variable region of a capture probe); and using the 3' end of the capture probe to extend across the region of genomic nucleic acid having a genetic event with one or more terminating base species, where if more than one is used each has a unique distinguishable label, e.g., label 1 for base A, label 2 for base T, label 3 for base G, and label 4 for base C; thereby analyzing the amplified products.

In a preferred embodiment, at least one reaction step is performed on a three-dimensional array, e.g., a gel array.

Preferably, a hairpin primer has about 15–1500 nucleotides, and more preferably about 24–500 nucleotides and most preferably about 30–150 nucteotides.

The hairpin primer is constructed of DNA or RNA or analogs thereof. Preferably, the hairpin primer is constructed of DNA.

The polymerase enzyme can be any that affects the synthesis of the polymerase extended product.

In another aspect, the invention features a method of analyzing a polynucleotide, e.g., detecting a genetic event, e.g., a single nucleotide polymorphism, in a sample.

The method includes:

1. providing a sample which includes a sample polynucleotide sequence to be analyzed, said sample polynucleotide being at least partially single stranded and containing a region of recognizable sequence adjacent to the single stranded terminus;
2. (a) annealing an effective amount of sample sequence to a hairpin primer, wherein the hairpin primer comprises at least one copy of a nucleotide sequence complementary to the sequence of the sample polynucleotide sequence and optionally,
   (b) extending the hairpin primer with an effective amount of at least two types of nucleotide triphosphates and an effective amount of a polymerase enzyme to yield a product, e.g., a single stranded polymerase extended product complementary to a substantial portion of the single stranded region of the sample polynucleotide; and
   (c) optionally, amplifying the polymerase extended product to produce amplified products, herein termed amplified products;
   (e) cleaving the amplified products with a restriction enzyme, e.g., a type IIs restriction enzyme;
3. (a) annealing an effective amount of cleaved amplified products (from 2e) to at least one copy of a positioning oligonucleotide having a 5' nucleotide sequence complementary to a portion of the sequence comprising the 3' end of the cleaved amplified products and a 3' nucleotide sequence complementary to a portion of the sequence comprising the 5' end of the cleaved amplified products wherein the 5' end and the 3' end of the cleaved amplified products are positioned so as to abut each other; and
   (b) joining the 5' end and the 3' end of the cleaved amplified products to yield a circular oligonucleotide template and optionally,
   (c) combining the circular template with an effective amount of a RCA primer, at least two types of nucleotide triphosphates and an effective amount of a polymerase enzyme to yield a product, e.g., a single stranded oligonucleotide multimer complementary to the circular oligonucleotide template; and
   (d) optionally, cleaving the product to produce cleaved amplified product
4. analyzing product from 3 b, c, or d, by providing an array of a plurality of capture probes, wherein each of the capture probes is positionally distinguishable from other capture probes of the plurality on the array, and wherein each positionally distinguishable capture probe includes at least one unique (i.e., not repeated in another capture probe) region, optionally, adjacent to a common (i.e., repeated in all the capture probes) region;

hybridizing the amplified products with the array of capture probes, thereby analyzing the sample sequence.

In preferred embodiments, analyzing a sample polynucleotide includes, e.g., sequencing the polynucleotide sequence, e.g., by sequencing by hybridization or positional sequencing by hybridization, detecting the presence of, or identifying a genetic event, e.g., a SNP, in a target nucleic acid, e.g., a DNA.

In preferred embodiments, the genetic event is within 12 bases, more preferably within 1, 2, 3, 4, 5, or 6 bases in the single stranded portion of sample polynucleotide that is adjacent to and immediately follows the double stranded region; more specifically, in the region of the single stranded portion of the sample polynucleotide farthest from the single stranded terminus, or is sufficiently close to the double strand portion of the sample polynucleotide that a mismatch would inhibit DNA polymerase-based extension from the sample polynucleotide/hairpin primer complex.

In equally preferred embodiments, the genetic event is located anywhere within the single stranded portion of the sample polynucleotide.

In preferred embodiments, the target polynucleotide in the sample is amplified, e.g., by PCR, prior to contact with a hairpin primer.

In preferred embodiments, the hairpin primer includes a site for a type 2s restriction enzyme and the site is positioned, e.g., such that a type 2s restriction enzyme binding at the site cleaves adjacent the region which binds the sample sequence or cleaves in the region which binds the sample sequence.

In a preferred embodiment, a region of the hairpin primer is complementary to a genetic event, e.g., a mutation or SNP, and hybridizes effectually to sample nucleic acid having the event and sample nucleic acid not having the event.

In preferred embodiments the polynucleotide sequence is: a DNA molecule: all or part of a known gene; wild type DNA; mutant DNA; a genomic fragment, particularly a human genomic fragment; a cDNA, particularly a human cDNA.

In preferred embodiments the polynucleotide sequence is: an RNA molecule: nucleic acids derived from RNA transcripts; wild type RNA; mutant RNA, particularly a human RNA.

In preferred embodiments the polynucleotide sequence is: a human sequence; a non-human sequence, e.g., a mouse, rat, pig, primate.

In preferred embodiments the method is performed: on a sample from a human subject; and a sample from a prenatal subject, as part of genetic counseling; to determine if the individual from whom the target nucleic acid is taken should receive a drug or other treatment; to diagnose an individual for a disorder or for predisposition to a disorder; to stage a disease or disorder.

In preferred embodiments the capture probes are single stranded probes in an array.

In preferred embodiments the capture probes have a structure comprising a double stranded portion and a single stranded portion in an array.

In preferred embodiments hybridization to the array is detected by mass spectrophotometry, e.g., by MALDI-TOF mass spectrophotometry.

In a preferred embodiment the amplified products (amplified products) which hybridizes to a capture probe, or the capture probe, is the substrate of or template for an enzyme mediated reaction.

For example, after hybridization to the capture probe, the amplified products is ligated to the capture probe, or after the hybridization it is extended along the capture probe.

In preferred embodiments the method includes one or more enzyme mediated reactions in which a nucleic acid used in the method, e.g., an amplified products, a capture probe, a sequence to be analyzed, or a molecule which hybridizes thereto, is a substrate or template for the enzyme mediated reaction. The enzyme mediated reaction can be: an extension reaction, e.g., a reaction catalyzed by a polymerase; a linking reaction, e.g., a ligation, e.g., a reaction catalyzed by a ligase; or a nucleic acid cleavage reaction, e.g., a cleavage catalyzed by a restriction enzyme, e.g., a Type IIs enzyme or an exonuclease. The amplified products which hybridizes with the capture probe can be the substrate in an enzyme mediated reaction, e.g., it can be ligated to a strand of the capture probe. Alternatively, the capture probe can be extended along the hybridized amplified products. (Any of the extension reactors discussed herein can be performed with labeled, or chain terminating, subunits). The capture probe duplex can be the substrate for a cleavage reaction. These reactions can be used to increase the specificity of the method or to otherwise aid in detection, e.g., by providing a signal.

Methods of U.S. Pat. No. 5,503,980 and U.S. Pat. No. 5,631,134, both of which are hereby incorporated by reference can be used herein, particularly, the array and array-related steps recited herein can use methods taught in these patents.

In preferred embodiments, the method includes providing an array having a plurality of capture probes, wherein each of the capture probes is a) positionally distinguishable from the other capture probes of the plurality and has a unique variable region (not repeated in another capture probe of the plurality), b) has a variable region capable of hybridizing adjacent to the genetic event; and has a 3' end capable of serving as a priming site for extension; hybridizing the amplified products having a genetic event to a capture probe of the array, (preferably the region of the amplified products having a genetic event hybridizes adjacent to the variable region of a capture probe); and using the 3' end of the capture probe to extend across the region of genomic nucleic acid having a genetic event with one or more terminating base species, where if more than one is used each has a unique distinguishable label, e.g., label 1 for base A, label 2 for base T, label 3 for base G, and label 4 for base C; thereby analyzing the amplified products.

In a preferred embodiment, at least one reaction step is performed on a three-dimensional array, e.g., a gel array.

Preferably, a hairpin primer has about 15–1500 nucleotides, and more preferably about 24–500 nucleotides and most preferably about 30–150 nucleotides.

The hairpin primer is constructed of DNA or RNA or analogs thereof. Preferably, the hairpin primer is constructed of DNA.

The polymerase enzyme can be any that affects the synthesis of the polymerase extended product.

In another aspect, the invention features a method of analyzing a polynucleotide, e.g., detecting a genetic event, e.g., a single nucleotide polymorphism, in a sample.

The method includes:

1. providing a sample which includes a sample polynucleotide sequence to be analyzed, said sample polynucleotide being at least partially single stranded and containing a region of recognizable sequence adjacent to the single stranded terminus;
2. (a) annealing an effective amount of sample sequence to a hairpin primer, wherein the hairpin primer comprises at least one copy of a nucleotide sequence complementary to the sequence of the sample polynucleotide sequence and optionally,
    (b) extending the hairpin primer with an effective amount of at least two types of nucleotide triphosphates and an effective amount of a polymerase enzyme to yield a product, e.g., a single stranded polymerase extended product complementary to a substantial portion of the single stranded region of the sample polynucleotide; and
    (c) optionally, amplifying the polymerase extended product to produce amplified products, herein termed amplified products;
    (d) hybridizing a first set of amplified products derived from a first sample polynucleotide(s) with a second set of amplified products derived from a second sample polynucleotide(s);
    (e) separating duplexes from (d) containing mismatches from perfectly matched duplexes;
3. analyzing mismatched duplexes from (e) by providing an array of a plurality of capture probes, wherein each of the capture probes is positionally distinguishable from other capture probes of the plurality on the array, and wherein each positionally distinguishable capture probe includes at least one unique (i.e., not repeated in another capture probe) region, optionally, adjacent to a common (repeated in all the capture probes) region; thereby analyzing the sample sequence.

In preferred embodiments, analyzing a sample polynucleotide includes, e.g., sequencing the polynucleotide sequence, e.g., by sequencing by hybridization or positional sequencing by hybridization, detecting the presence of, or identifying a genetic event, e.g., a SNP, in a target nucleic acid, e.g., a DNA.

In preferred embodiments, the genetic event is within 12 bases, more preferably within 1, 2, 3, 4, 5, or 6 bases in the single stranded portion of sample polynucleotide that is adjacent to and immediately follows the double stranded region; more specifically, in the region of the single stranded portion of the sample polynucleotide farthest from the single stranded terminus, or is sufficiently close to the double strand portion of the sample polynucleotide that a mismatch would inhibit DNA polymerase-based extension from the sample polynucleotide/hairpin primer complex.

In preferred embodiments, the genetic event is located anywhere within the single stranded portion of the sample polynucleotide.

In preferred embodiments, the target polynucleotide in the sample is amplified, e.g., by PCR, prior to contact with a hairpin primer.

In preferred embodiments, the hairpin primer includes a site for a type 2s restriction enzyme and the site is positioned, e.g., such that a type 2s restriction enzyme binding at the site cleaves adjacent the region which binds the sample sequence or cleaves in the region which binds the sample sequence.

In a preferred embodiment, a region of the hairpin primer is complementary to a genetic event, e.g., a mutation or SNP, and hybridizes effectually to sample nucleic acid having the event and sample nucleic acid not having the event.

In preferred embodiments the polynucleotide sequence is: a DNA molecule: all or part of a known gene; wild type DNA; mutant DNA; a genomic fragment, particularly a human genomic fragment; a cDNA, particularly a human cDNA.

In preferred embodiments the polynucleotide sequence is: an RNA molecule: nucleic acids derived from RNA transcripts; wild type RNA; mutant RNA, particularly a human RNA.

In preferred embodiments the polynucleotide sequence is: a human sequence; a non-human sequence, e.g., a mouse, rat, pig, primate.

In preferred embodiments the method is performed: on a sample from a human subject; and a sample from a prenatal subject, as part of genetic counseling; to determine if the individual from whom the target nucleic acid is taken should receive a drug or other treatment; to diagnose an individual for a disorder or for predisposition to a disorder; to stage a disease or disorder.

In preferred embodiments the capture probes are single stranded probes in an array.

In preferred embodiments the capture probes have a structure comprising a double stranded portion and a single stranded portion in an array.

In preferred embodiments hybridization to the array is detected by mass spectrophotometry, e.g., by MALDI-TOF mass spectrophotometry.

In a preferred embodiment the amplified products (amplified products) which hybridizes to a capture probe, or the capture probe, is the substrate of or template for an enzyme mediated reaction.

For example, after hybridization to the capture probe, the amplified products is ligated to the capture probe, or after the hybridization it is extended along the capture probe.

In preferred embodiments the method includes one or more enzyme mediated reactions in which a nucleic acid used in the method, e.g., an amplified products, a capture probe, a sequence to be analyzed, or a molecule which hybridizes thereto, is a substrate or template for the enzyme mediated reaction. The enzyme mediated reaction can be: an extension reaction, e.g., a reaction catalyzed by a polymerase; a linking reaction, e.g., a ligation, e.g., a reaction catalyzed by a ligase; or a nucleic acid cleavage reaction, e.g., a cleavage catalyzed by a restriction enzyme, e.g., a Type IIs enzyme or an exonuclease. The amplified products which hybridizes with the capture probe can be the substrate in an enzyme mediated reaction, e.g., it can be ligated to a strand of the capture probe. Alternatively, the capture probe can be extended along the hybridized amplified products. (Any of the extension reactors discussed herein can be performed with labeled, or chain terminating, subunits). The capture probe duplex can be the substrate for a cleavage reaction. These reactions can be used to increase the specificity of the method or to otherwise aid in detection, e.g., by providing a signal.

Methods of U.S. Pat. No. 5,503,980 and U.S. Pat. No. 5,631,134, both of which are hereby incorporated by reference can be used herein, particularly, the array and array-related steps recited herein can use methods taught in these patents.

In preferred embodiments, the method includes providing an array having a plurality of capture probes, wherein each of the capture probes is a) positionally distinguishable from the other capture probes of the plurality and has a unique variable region (not repeated in another capture probe of the plurality), b) has a variable region capable of hybridizing adjacent to the genetic event; and has a 3' end capable of serving as a priming site for extension; hybridizing the amplified products having a genetic event to a capture probe of the array, (preferably the region of the amplified products having a genetic event hybridizes adjacent to the variable region of a capture probe); and using the 3' end of the capture probe to extend across the region of genomic nucleic acid having a genetic event with one or more terminating base species, where if more than one is used each has a unique distinguishable label, e.g., label 1 for base A, label 2 for base T, label 3 for base G, and label 4 for base C; thereby analyzing the amplified products.

In a preferred embodiment, at least one reaction step is performed on a three-dimensional array, e.g., a gel array.

Preferably, a hairpin primer has about 15–1500 nucleotides, and more preferably about 24–500 nucleotides and most preferably about 30–150 nucleotides.

The hairpin primer is constructed of DNA or RNA or analogs thereof. Preferably, the hairpin primer is constructed of DNA.

The polymerase enzyme can be any that affects the synthesis of the polymerase extended product.

In another aspect, the invention features, a hairpin primer. The probe includes, preferably in a 5' to 3' orientation:

a first nucleic acid contacting region which is complementary to a first portion of a target nucleic acid;

a double stranded region, comprised of complementary base pairing of a portion of the hairpin primer oligonucleotide near its 5' end with a portion of the same oligonucleotide near its 3' end;

optionally, at least one single-stranded region;

a second nucleic acid contacting region that is complementary to a second portion of the target nucleic acid.

In preferred embodiments, the elements are in the recited order.

In specific embodiments, one or more nucleotides in the first nucleotide contacting region or second nucleotide contacting region may be designed to contain degenerate nucleotides.

In preferred embodiments, the first nucleotide contacting region is 4–12 nucleotides long.

In preferred embodiments, the double stranded region is 4–20 nucleotides long.

In preferred embodiments, the single stranded region is 4–12 bases long.

In preferred embodiments, the second nucleic acid contacting region is 4–12 bases long.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable materials and methods are described below. All publications, patent applications, patents and other references mentioned herein are incorporated by reference in their entirety. In case of conflict, the present specification, including definitions will control. In addition, the materials, methods, and examples are illustrative only and not intended to be limiting.

Other features and advantages of the invention will be apparent from the following detailed description.

BRIEF DESCRIPTION OF THE DRAWINGS

FIGS. 5 & 6 are schematic drawings of amplification of the polymerase extended product and product thereof

DETAILED DESCRIPTION

Figure 1:
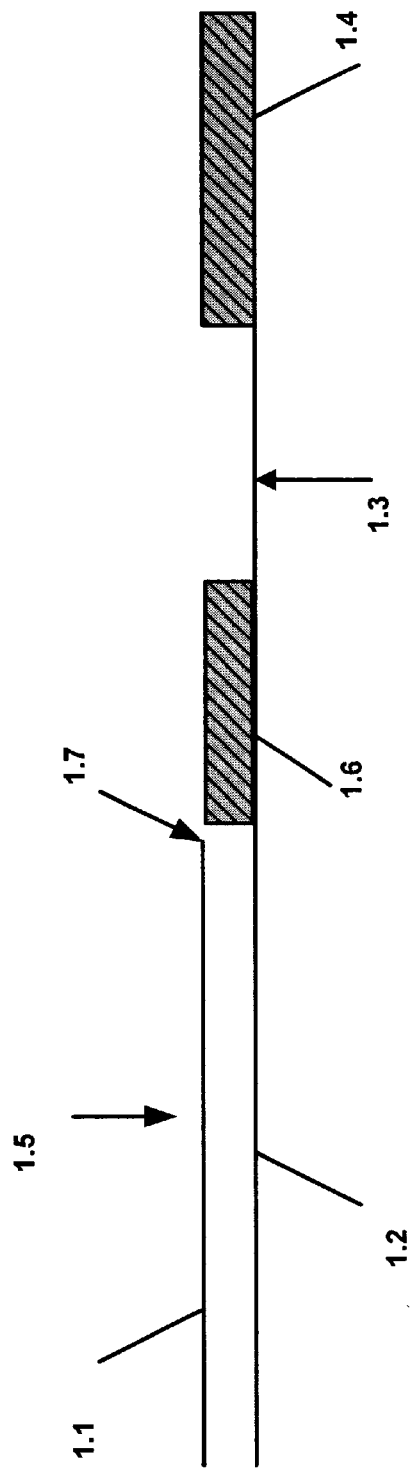
FIG. 1 is a schematic drawing of a target polynucleotide

This invention relates to methods and devices for identifying and quantifying nucleic acids in a sample of nucleic acids, in particular, to methods of genomics analysis. Accordingly, this invention can be applied to analysis of gene expression by identifying and quantifying complementary DNA ("cDNA") and to genetic analysis by identifying and quantifying genomic DNA ("gDNA").

The methods of this invention observe the presence of sets of composite subsequences, comprising nucleotides in the nucleic acids of the sample ("composite subsequences"), in general, starting with a possibly complex sample of nucleic acids, preferably DNAs. The preferred methods then determine which sequences have the observed subsequence sets and which observed subsequence sets are not present in any sequence in the database of nucleic acids that may be present in the original sample. Accordingly, nucleic acids in the original sample are either identified or marked as possibly novel. In preferred embodiments, the methods of this invention identify the presence of composite subsequence sets in order that nucleic acids can in turn be quantitatively identified.

A composite subsequence set includes at least two adjacent nucleotide subsequences in a nucleic acid. In preferred embodiments, a composite subsequence comprises a first subsequence and a second subsequence adjacent to the first subsequence. In turn, the composite subsequence is adjacent to a first recognizable sequence and spaced apart from a second recognizable sequence by a variable number of nucleotides. In preferred embodiments, a composite subsequence may comprise of one or more additional nucleotides between the first and second subsequences.

In a preferred embodiment, the methods of this invention observe the first and second subsequences sequentially in at least two steps. In the first observational step, the preferred methods first produce one or more limited-complexity subsamples of nucleic acid fragments, each nucleic acid in a subsample being derived from those nucleic acids in the original sample, which include the second recognizable sequence. In preferred embodiments, more than one second recognizable sequences may be employed singly or in combination to generate the nucleic acid fragments in the subsample. These subsamples are produced from the original sample in a manner that is repeatable and results in predictable fragments. The choice of second recognizable sequences is employed in a manner that the subsamples collectively represent most or all of the original nucleic acid in the sample.

Next, the preferred methods of the invention convert substantially all of the fragments in each subsample into partially single stranded nucleic acid fragments, i.e., a nucleic acid fragment containing a double stranded portion and a single stranded overhang. The observational methods of this invention then observe composite subsequences present in each partially single stranded fragment of the subsample. In preferred embodiments, a plurality of partially single stranded fragments is produced from each fragment in the subsample. The composite subsequence is located in the single stranded overhang immediately adjacent to the double stranded portion and the second recognizable sequence is located at the terminus of the single stranded overhang. The first recognizable sequence is located at the terminus of the double stranded portion that is closest to the composite subsequence. In preferred embodiments, the first recognizable sequence and the 3'-most nucleotide of the composite subsequence are adjacent to each other, and the second recognizable sequence is closest to the second subsequence, being spaced apart from the second subsequence by a variable number of nucleotides. In other words, the single stranded portion of the partially single stranded fragment is a structure that is bounded at the junction of single- and double-stranded region by the composite subsequence and at its 5'-terminus by the second recognizable sequence. Thus, a plurality of partially single stranded fragments derived from any single fragment in the subsample will contain a plurality of composite subsequences. This invention is equally adaptable to the partially single stranded fragment containing a similar structure at the opposite terminus of the nucleic acid fragment. In this case, one or both subsequences may be observed simultaneously or sequentially by the methods of this invention. In preferred embodiments, one subsequence is observed per partially single stranded fragment.

In the second step, the methods of this invention comprise computer-implemented nucleic acid database searches, which determine less than 5–10, and preferably only one, candidate sequences that could produce a fragment in the predictable manner and that also includes the particular composite subsequence or part thereof.

The methods of this invention also relate to devices that allow the rapid and high throughput determination of the composite subsequences without requiring conventional cloning and/or sequencing or cumbersome electrophoretic separations, and to the methods for use of such devices. These devices are based on novel implementations of arrays of oligonucleotides preferably attached to a surface. The arrays of this invention are adapted to the specific and reliable determination of short single stranded subfragments derived from the subsample, and include the second subsequences adjacent to an adapter sequence, which is the same in all subsets. Reliability is enhanced by the use of enzymatic recognition of correct hybridization, such as by ligation or polymerase extension. Advantageously, these arrays permit the parallel and quantitative determination of the composite subsequences in all the fragments of a subsample without the need to separate the individual fragments.

In the following, the methods of the present invention are described first followed by a description of the arrays of this invention and their methods of use.

Methods for Target Subsample Preparation

Generally, the method of identifying the presence of a nucleic acid in a sample containing one or more nucleic acids, proceed, first by observing or recognizing a nucleotide subset ("composite subsequence") in a nucleic acid of the sample, and second, by identifying such a nucleic acid by reference to a database of nucleic acids that may be present in the sample. Preferably, the composite subsequence consists of two subsequences, a first subsequence and a second subsequence.

This section describes general requirements on the composite subsequence, and various applications of the general methods of this invention. Next this section describes the general methods for preparation of target subsample starting from one or more nucleic acids present in the sample, including generation of subsamples of nucleic acid fragments from original nucleic acids in the sample, and determination of the first and second subsequences.

General Methods for Target Sample Preparation:

Turning now to a preferred structure for composite subsequence sets, FIG. 1 generally illustrates a nucleic acid fragment 1.5, derived from the nucleic acids contained in the sample. Nucleic acid 1.5 is partially single stranded, composed of two strands, 1.1 hybridized to 1.2. The positional constraints include the following. The single stranded portion of 1.2, 1.3 contains at its free terminus, the second recognizable region, 1.4. The composite subsequence, 1.6, is located in the single stranded portion of 1.3, and is located adjacent to the junction of the single- and double stranded regions of 1.5. The first recognizable sequence, 1.7, is located at the terminus of 1.1, adjacent to 1.6. In this configuration, the single stranded portion 1.3, contains, in order starting from the junction of single and double stranded regions, the first recognizable sequence 1.7, the composite subsequence, 1.6, a variable number of nucleotides, and the second recognizable sequence, 1.4.

According to this invention, the nucleic acid fragment 1.5 can be any length, ranging from less than 100 bases to 50 kilobases (kb) or more. In preferred embodiments, 1.5 is 100 bases to 5 kb in length. In preferred embodiments, 1.5 contains an anchorable moiety. In preferred embodiments, the composite subsequence is 40 bases long, more preferably 20 bases long, most preferably 12 bases long. In preferred embodiments, the composite subsequence is composed of a first subsequence and a second subsequence. The first subsequence is preferably located adjacent to the second subsequence, and is 30 or more nucleotides long, more preferable 20 nucleotides long, more preferable less than 10 nucleotides long, and most preferably 4 to 8 nucleotides long. In preferred embodiments, the second subsequence is 12 or more nucleotides long, more preferable 8 nucleotides long and most preferable 4 to 7 nucleotides long.

The first recognizable sequence, 1.7 is the free terminus of 1.1 adjacent to the composite subsequence, 1.6. In preferred embodiments, 1.7 comprises at least the terminal nucleotide of 1.1. In equally preferred embodiments, 1.7 is an oligonucleotide, herein termed an anchoring oligonucleotide, that hybridizes adjacent to the composite subsequence. The anchoring oligonucleotide can be any length, and is preferably 50 or more nucleotides, more preferably 30 nucleotides, more preferably 20 nucleotides and most preferably, less than 10 nucleotides in length. The second recognizable sequence, 1.4, located at the free terminus of the single stranded portion 1.3, is any selected sequence, such as an adapter that can be ligated to the terminus of a nucleic acid fragment.

For the sake of illustration only, and without limitation, the preferred methods of the invention for the generation of a subsample containing a plurality of fragments of the type described in FIG. 1 from the original nucleic acids in the sample are now described. First, the logical steps of the preferred observational methods of this invention are described in relation to an exemplary nucleic acid sample, human genomic DNA, and a preferred example is provided in Example 1. For the sake of this invention, human genomic DNA is taken to consist of 3 billion base pairs. From a probabilistic view, any contiguous sequence of six bases, such as the recognition site of a restriction endonuclease, will appear in this DNA sample a number of times equal to 4 raised to the power of the number of nucleotides in the sequence set, which is 6. Thus, the 6-mer sequence will appear, on average, once every 4096 base pairs. When the sample is digested completely with restriction endonuclease, the expected number of fragments is the total size of the nucleic acid divided by 4096, which in this example is 732,422 fragments. While the predicted size of the fragments is 4096, it is clear to one of ordinary skill in the art that, in practice, a smear of fragments are observed, which may range in size from a few hundred base pairs up to tens of kilobases. However, the actual sizes of the fragments and the variations between sizes of fragment within the same subsample of nucleic acid fragments are of little significance to this invention.

Next, the methods of this invention determine the presence of a composite subsequence, or its absence, in one or more nucleic acid fragments of the subsample. By way of example, the preferred methods are herein described in relation to a composite subsequence of 8 bases. A selected 8-base sequence is expected to appear once every 256,000 bases, which is derived by solving for 4 raised to the power 8. Such a sequence is expected to occur 23,400 times in human genomic DNA, i.e., on average, in one out of every 30 fragments of the 732,422 fragments obtained by the aforementioned subsample. Thus the total number of fragments expected to contain the subsequence are 23,626, which is far too many to be determined by conventional experimental methods. However, from the same arguments, any chosen 11 base sequence is expected only 1,500 times in genomic DNA. Thus, the total number of fragments expected to contain the subsequence is only 488. Therefore, it is an objective of this invention, to apportion the fragments of the subsample by setting positional constraints for determination of the composite subsequence. The preferred methods of this invention convert fragments of the subsample in to partially single stranded fragments by exonuclease digestion of subfragments derived by endonuclease digestion in two steps: first, ligation of an adapter sequence with single stranded ends complementary to the predictable single stranded overhangs on fragments left by restriction endonuclease digestion, and second, digestion with an exonuclease. In preferred methods the exonuclease is one that removes nucleotides sequentially from the 3' end of one strand of a double stranded or partially double stranded nucleic acid fragment. A preferred enzyme that performs this function is Exonuclease III (Stratagene, La Jolla, Calif.), which catalyzes the step-wise, non-processive, 3' to 5' removal of 5'-mononucleotides from double-stranded DNA with a free 3'-hydroxyl (—OH) end. Other preferred enzymes include, but are not limited to, S1 nuclease, DNaseI, Bal31, mung bean nuclease, P1 nuclease, lambda exonuclease, restriction endonuclease, RNaseH, and RNaseI. It is readily apparent to one of skill in the art that the length of single stranded portions of the product from exonuclease digestion is a function of the concentration of exonuclease in the reaction, or length of incubation, temperature, concentrations of reaction components and so on. The preferred methods of this invention take into account these considerations. Further, the preferred methods seek to create partially single stranded fragments of nucleic acids in the subsample, wherein the length of single stranded portions of the partially single stranded fragments is same or comparable in most or all of the fragments in the subsample due to exonuclease activity being relatively independent of sequence composition, the number of fragments and the length of the substrate nucleic acid fragment. However, fragmented target nucleic acids are predicted to have a distribution of nucleic acids in the junction of double and single stranded regions of partially single stranded fragments which is sufficiently broad so that the nucleotide sequences of the fragments in the subsample will include the entire sequence of the target nucleic acid. The predicted occurrence of the composite subsequence in the partially single stranded fragments of an exemplary subsample wherein the single stranded portions range about 300 nucleotides in length is now described. The occurrence of the exemplary 11 base sequence in the aforementioned subsample of partially single stranded fragments is derived by the following equation:

$$\frac{\text{Length of single stranded portion} \times \text{Number of fragments}}{\text{Frequency of occurrence of composite subsequence}}$$

which is, $$\frac{300 \times 732{,}422}{4{,}000{,}000}$$

or, 55 fragments.

Further, if the composite subsequence were only 5 bases in length, the predicted number of partially single stranded fragments in the exemplary subsample is:

$$\frac{300 \times 732{,}422}{1{,}024}$$

or, 214,577 fragments.

In one aspect, this invention features positional constraints to the location of the composite subsequence. In preferred methods, the composite subsequence is located in the single stranded portion adjacent to the junction of single and double stranded portions of partially single stranded fragments of the subsample, wherein the first recognizable sequence is the terminal nucleotide of the double stranded portion of the junction. The predicted number of partially single stranded fragments in the foregoing exemplary subsample wherein the composite subsequence is located in the junction is now described. Of the 732,422 fragments, only one in 4 fragments will contain a T at the first position of the single stranded portion of the junction, only one in 16 fragments will contain a TT at the first and second positions of the junction, only one in 64 will contain a TTT, and so on. It follows that only one in 1024 fragments will contain a specified 5 base sequence in the junction. In this case, the length of the single stranded overhang does not affect the prediction. The number of fragments in the exemplary subsample of partially single stranded fragments containing a 5 base composite sequence, or part thereof, at the junction of single and double stranded portions is determined from the equation:

$$\frac{732{,}422}{1{,}024}$$

or, 715 fragments.

Thus, the preferred methods of the invention detail a fragmentation process whereby the number of fragments is reduced to a manageable size. From the same arguments, the number of fragments can be reduced to only 178 if the length of the composite subsequence, or part thereof, is increased by one base to 6 nucleotides. Of the 715 fragments for a 5 base composite subsequence, the probability of occurrence of a different one of a selected 5 base sequence adjacent to it is 715 divided by 1024, which is less than one. Thus, the probability that a subsequence in each of the 715 fragments can be unambiguously determined by fractionating or separating the fragments is high. In preferred methods of this invention, the first subsequence of the composite subsequence is at least 5–6 bases which is adjacent to the second subsequence which, in turn, is in the range of 5–6 bases in length. The predicted total amount of nucleotides of nucleic acid fragments sampled in a single iteration is 715 fragments×1024 nucleotides (wherein the second subsequence is 5 nucleotides in length)=732,160. This invention is adaptable to iterations of the determination process in 96 or 384 formats wherein different subsets of composite subsequences are determined. The predicted total number of nucleotides sampled in such determinations are 70,287,360 and 281,149,440, representing 1% and 4% respectively, of human genomic nucleic acid. Further, the methods of this invention implicate the remainder of the fragments (732,160−715=731,445) as not containing the composite subsequence. Thus, the total amount of information obtained is enormous.

This invention is equally adaptable to cDNA analysis, in particular, to gene expression analysis. The human genome contains an estimated 100,000 genes, of which as many as 30,000 are believed to be expressed in any single complex tissue. For the sake of this invention, the average size of a mRNA in human samples is taken to be 3000 nucleotides in length. Thus, the total nucleotide composition of human mRNA population from a complex tissue is derived by multiplying 3000 by the number of mRNAs expressed in a complex tissue, or 90,060,000 nucleotides. It follows from the foregoing, that the methods of this invention can sample all of, or even greatly oversample the estimated total nucleotide complexity of mRNA populations from human samples.

In another aspect, the partially single stranded fragments of the invention feature an anchoring nucleotide, wherein the anchoring nucleotide hybridizes adjacent to the composite subsequence. In this aspect, the partially single stranded nucleic acids are derived, following restriction endonuclease digestion and ligation of adapter, by denaturing nucleic acid fragments and hybridizing the anchoring oligonucleotide. The predicted number of fragments derived in this manner are herein described in relation to foregoing arguments of exemplary sample of human genomic DNA. The predicted number of occurrences of a selected 6 base sequence in human genomic DNA is 6,000,000,000 divided by 4 raised to the power of 6, which is 1,464,844. Of these, the number of fragments wherein the subsequence is adjacent to another selected 6 base sequence is only 357. From size considerations, each of the 1,464,844 denatured fragments following restriction endonuclease digestion and adapter ligation are likely to contain at least one occurrence hybridizable to the 6 base anchoring oligonucleotide to single stranded fragments, thereby being implicated by the presence or absence of the composite subsequence or part thereof. The preferred methods of this invention take into consideration these aspects for determining the composite subsequence.

Figure 2:
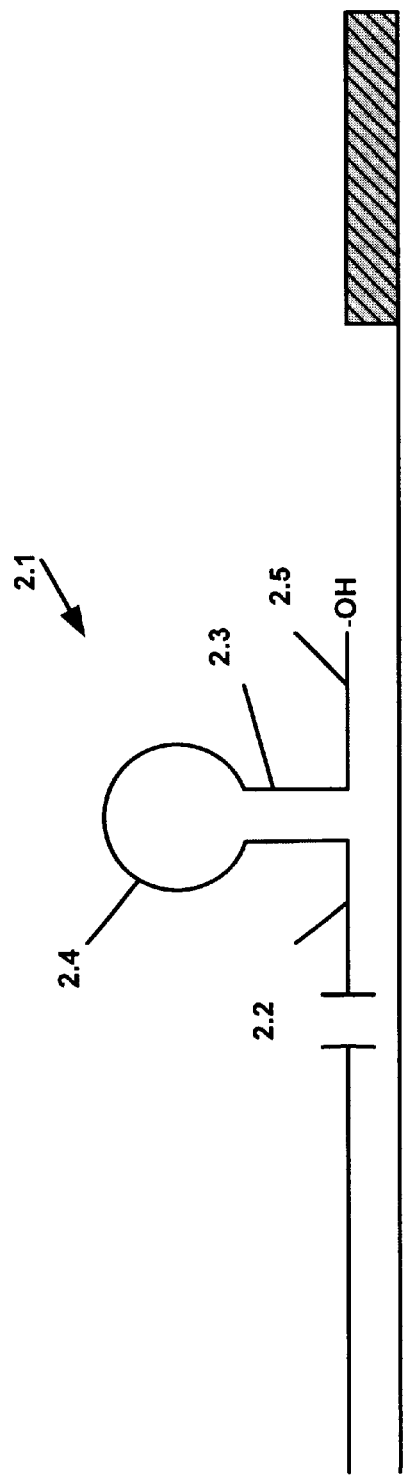
FIG. 2 is a schematic drawing of a hairpin primer hybridized to the target.

In another aspect, this invention features a hairpin primer that hybridizes to partially single stranded nucleic acid fragments and serves as a primer for extension by a nucleic acid polymerase that utilize the single stranded portion of fragments as template. The structure of the hairpin primer is herein described in relation to FIG. 2. In preferred embodiments, the hairpin primer, 2.1, is a single strand of oligonucleotides, comprising, in order, from 5' to 3' orientation, a first nucleic acid contacting region, 2.2, a first stem region, optionally, at least one loop region, 2.4, comprising single-stranded nucleotides, a second stem region, 2.3, comprising a nucleotide sequence that is hybridizable to the nucleotides of the first stem region so as to form a duplex, a second nucleic acid contacting region, 2.5. In preferred embodiments, the elements are in the recited order. In preferred embodiments, the 3' terminal nucleotide of 2.1 contains a free —OH moiety.

The hairpin primer can be of any length, but preferably is about 15–1500 nucleotides in length, and more preferably about 24–500 nucleotides and most preferably about 30–150 nucleotides. In preferred embodiments, the first nucleotide contacting region is 4–12 nucleotides long, the first and second stem regions each is 4–20 nucleotides long. In preferred embodiments, the single stranded region is 4–12 bases long and the second nucleic acid contacting region is 4–12 bases long. In preferred embodiments, the hairpin primer may contain randomized nucleotide positions in one or more regions, preferably in regions 2.2 or 2.5. According to this invention, randomized nucleotide position consists of the occurrence of more than one base in the selected position. For instance, in the sequence AANT, N is a randomized position, wherein A, T, C, or G base may occur at the said position indicating that a subset of hairpin primers will have A, another subset in the same population with have T at the indicated position, and so on. Further, the degree of randomization may be selected empirically, i.e., if 25% randomization is chosen then one out of 4 primers in the primer population will contain an A, T, C, or G. However, particular combinations may also be selected, e.g., 10%A; 30%T; 50%C; 20%G or other combinations, or may only select 2 or 3 nucleotides.

According to this invention, the hairpin primer hybridizes to the single stranded portion in the junction of single and double stranded regions of the partially single stranded nucleic acid fragment, 1.5, such that the first nucleotide of region 2.2 of the hairpin primer and the first recognizable sequence abut each other. In this configuration, region 2.2 hybridizes to and interrogates nucleotides in the first subsequence, and region 2.5 of the hairpin primer hybridizes to and interrogates the second subsequence. In preferred embodiments, the 3' terminal nucleotide of the first subsequence and the 5' most nucleotide of the second subsequence are adjacent nucleotides in the sample nucleic acid. It is preferred that the hairpin primer contains a recognition site for a restriction type of the type IIs variety, i.e., an endonuclease that cuts DNA outside of its recognition site. The type IIs site is preferably located in the stem region, more preferably in the second stem region. Further, the type IIs site may be positioned depending upon the functional attributes of the selected enzyme. In preferred embodiments, the site is positioned so as to cut the polymerase extended fragment outside of the second subsequence.

According to this invention, embodiments based on the use of hairpin primers include analyzing a sequence, e.g., to sequence the nucleic acid in question, or to identify SNPs, mutations and RNA molecules, or to clarify a sample, e.g., as to disease state, or generally in expression profiling or analysis.

Figure 3:
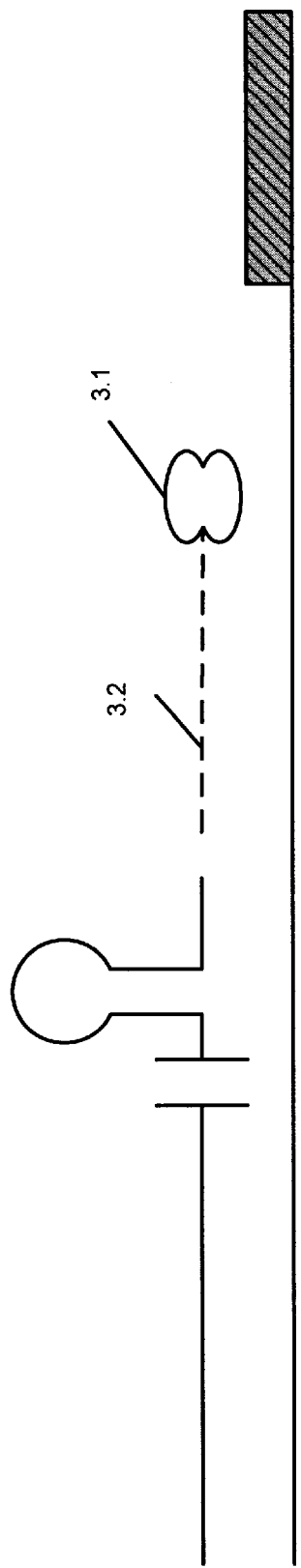
FIGS. 3 & 4 represent polymerase extension step and the product thereof

The hairpin primer hybridizes effectively at or near the genetic event in the target sequence, thereby providing a terminus for extension by the action of a polymerase, such as a DNA polymerase. Polymerase extension of the hairpin primer results in a single stranded polymerase extended product that is complementary in base sequence to a substantial portion of the single stranded region of the target polynucleotide. FIG. 3 depicts the hairpin primer being extended by a polymerase, 3.1, resulting in the production of extended product 3.2, using the single stranded region, 1.3 as a template. The polymerase employed for extension of the hairpin primer can be any that effect the template-dependent polymerization of nucleotides: it can be a DNA polymerase, an RNA polymerase, an RNA replicase, or a reverse transcriptase. Preferred polymerases include, but are not limited to, E. coli DNA polymerase, Klenow polymerase, Sequenase, T7 DNA polymerase, Bst polymerase and phi29 polymerase. Methods for the use of these and other nucleic acid modifying enzymes are described in Current Protocols in Molecular Biology (F. M. Ausubel et al., editors, John Wiley & Sons, 1989). Which is herein specifically incorporated by reference.

In preferred embodiments, the genetic event is within 12 bases, more preferably. within 1, 2, 3, 4, 5, or 6 bases in the single stranded portion of sample polynucleotide that is adjacent to and immediately follows the double stranded region; more specifically, in the region of the single stranded portion of the sample polynucleotide farthest from the single stranded terminus, or is sufficiently close to the double strand portion of the sample polynucleotide that a mismatch would inhibit DNA polymerase-based extension from the sample polynucleotide/hairpin primer complex.

Figure 4:
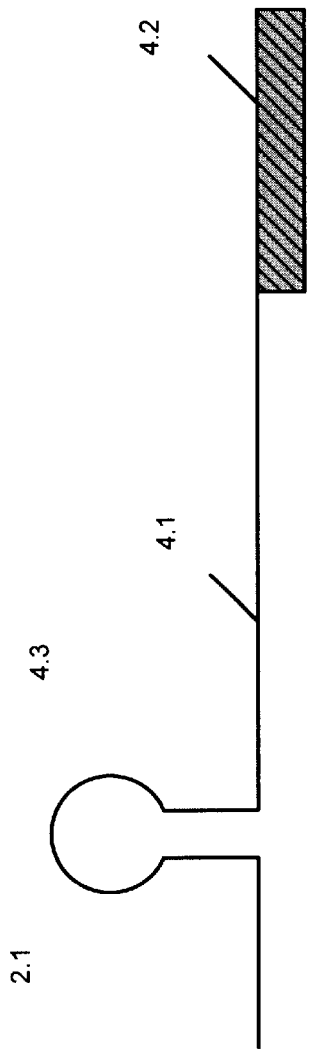
Figure 7:
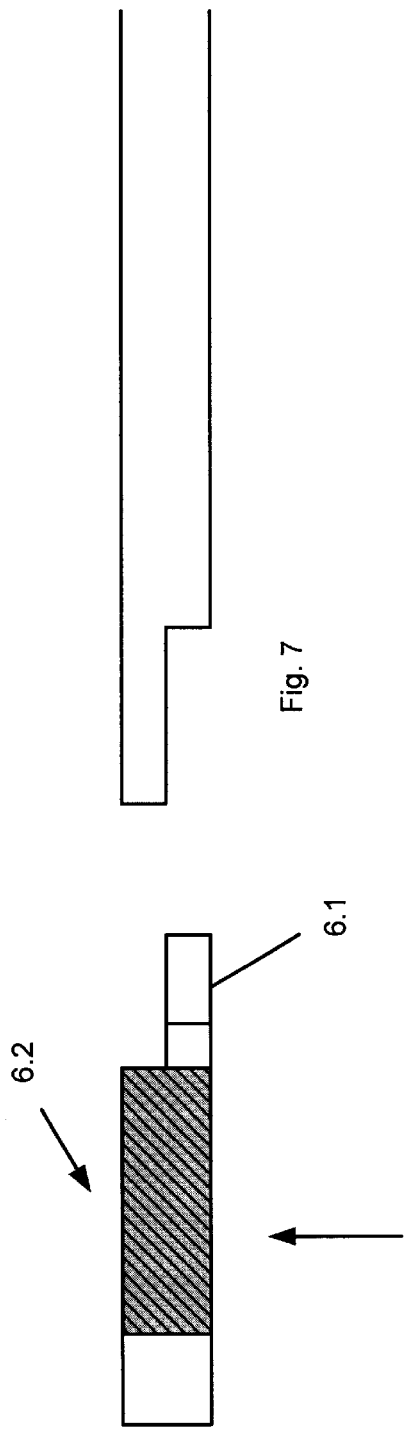
FIG. 7 is a schematic drawing of a cleavage product

The single stranded product, 4.3, of polymerase extension is shown in FIG. 4. It contains, in a 5' to 3' orientation, the hairpin primer, 2.1, a region 4.1, which is comprised of nucleotides that are complementary to the single stranded portion 1.3, of sample partially single stranded nucleotide, 1.5, and a region, 4.2, which is comprised of nucleotides that are complementary to region 1.4 of sample fragment. In this manner, the preferred target subsample preparation methods of this invention give rise to single stranded fragments in which the first subsequence and the second subsequence, that are located adjacent to each other in the sample target nucleic acids, are spaced apart in polymerase extended products by the nucleotides comprising the hairpin primer. Additionally, the second-subsequence is located adjacent to nucleotides of the hairpin primer, which are known sequences and which is the same in all subsets, instead of the first subsequences in the sample target nucleic acid fragments. The unique structure of the polymerase amplified products greatly facilitate the determination of the second subsequences.

In preferred embodiments, techniques are employed to improve hybridization specificity and strength of hairpin primer and partially single stranded fragments, especially in view of the lengths of the first and second nucleic acid contacting regions of the hairpin primer, which can each be as short as 4–6 nucleotides. Additionally, the hairpin primer hybridizes at the junction of the single and double stranded regions of partially single stranded fragments without gaps, wherein energetic base stacking interactions between the termini of hairpin primer and the terminal nucleotide of the first recognizable sequence improve overall hybridized duplex stability. Due to the short lengths of the single stranded region of partially single stranded fragments, about 300 to 500 bases, the probability of occurrence of a second composite subsequence within the single stranded region of the same partially single stranded nucleic acid fragment is low to negligible, thereby preventing ambiguity in the identification and quantification of nucleic acid fragments in a subsample. This invention is adaptable to further strengthening and/or proofreading the hybridization of hairpin primer to partially single stranded fragments by ligation, wherein the terminal nucleotide of the first recognizable sequence is ligated to the hairpin primer.

This invention is equally adaptable to one or more nucleotides of at least one of the nucleotide contacting regions of the hairpin primer being degenerate, i.e., containing a mixture of hairpin primers wherein their exists a probability of finding at least two species of hairpin primers containing a different nucleotide at any specified location. The number and position of degenerate sites in the hairpin primer can be varied. Such oligonucleotides are easily synthesized on current oligonucleotide synthesizers, an automated DNA synthesizer, e.g., Applied Biosystems (Foster City, Calif.) models 381A or 380B, or like instrument, and one of ordinary skill in the art is familiar with methods of such synthesis. In preferred methods, the second nucleotide contacting region contains degenerate oligonucleotides.

In another aspect, the preferred methods of this invention include determining one or more nucleotides of the first recognizable sequence. For instance, after exonuclease digestion and removal of exonuclease activity, such as by heat treatment, the partially single stranded fragment subsamples can be divided into 4 portions and, for each portion, the 3' terminus at the double stranded portion of the junction can be extended by a polymberase in presence of a dideoxynucleotide triphosphate. In this manner, each target subsample can be labeled as ddA, ddC, ddG, ddT, subsamples, and can thus result in the determination of one nucleotide adjacent to the composite subsequence following the determination of the composite subsequences by the methods of this invention.

In another aspect, the first and second nucleotide contacting regions of hairpin primers hybridize to the first and second subsequences of the composite subsequence, respectively. In preferred embodiments, the presence of a single nucleotide mismatch between the first nucleotide contacting region and the first subsequence or the second nucleotide contacting region and the second subsequence produces sufficient destabilization of the hybridization of the hairpin primer to partially single stranded nucleotide fragment so as to prevent the formation of a polymerase extended product for said fragment from said subsample. The hairpin primer supports not only the hybridization of the 12 bases comprising the nucleotide contacting regions, but also the remainder of the molecule which include the stem regions and the loop region, which together comprise greater than 20–40 additional nucleotides. Thus, the hairpin is so designed that only a subset of bases comprising it are involved in hybridization. Therefore, any destabilization of hybridization due to non-complementary bases will sufficiently destabilize the bulky hairpin primer so as to shift the equilibrium of the hybridization reaction away from hybridization. In the absence of effectual hybridization no polymerase extended product will be formed. This should be contrasted with other methods described in the art wherein random or semi-random oligomers are employed for hybridization, wherein the kinetics of the hybridization are governed solely by the presence or absence of mismatches between probe and target. Such methods include the methods taught in U.S. Pat. No. 5,552,270, U.S. Pat. No. 6,013, 445, U.S. Pat. No. 5,925,525, U.S. Pat. No. 5,866,3305, and U.S. Pat. No. 599,672 that are herein specifically incorporated by reference. In other words, the production of a polymerase extended product is in an indicator that the first and second hybridization nucleotide contacting regions of the hairpin primer are properly hybridized to the first and second subsequences, respectively. Accordingly, the preferred methods of this invention determine the first subsequence by the production of polymerase extension products. The second subsequence is determined by hybridization to an array of capture probes as described below, thereby determining the composite subsequence.

In preferred embodiments, the single stranded product 4.3 is amplified. Amplification can be performed using any of the methods described in the art, such as PCR, NASBA, strand displacement amplification (SDA), or other. Preferred methods for amplification by polymerase chain reaction are herein described in relation to FIG. 5.2. A pair of primers is utilized, one primer, 5.2, that is complementary to region 4.2, and another 5.1, that has the same sequence as the single stranded region, 2.1, of the hairpin primer. Thus, PCR amplification of the fragments in the subsample is achieved with two generic primers. The structural attributes of PCR product, 6.1, is shown in FIG. 6. It contains the primer region, 5.1 adjacent to the second subsequence, 6.2. In preferred embodiments, the amplified fragments have a different structure than the polymerase extended products, which serve as template for their production. The amplified products are truncated replicas of polymerase extended products, lacking the first nucleotide contacting region and additional nucleotides of the hairpin primer. Further, the amplified products are complementary to most of the single stranded portion of the partially single stranded fragments, except that the first subsequence is replaced by a portion of the hairpin primer adjacent to the second subsequence, which is the same in all subsets.

The polymerase extended product, 4.3, or its double-stranded product can be fragmented, e.g., using a type IIs restriction enzyme, such that the DNA is cleaved at the beginning or end of the sequence comprising the second subsequence. According to this invention, the type IIs restriction enzyme recognition sequence may be positioned along the length of the hairpin primer, polymerase extended product, or other, such as PCR primer, so as to allow a choice of cleavage site(s).

The dsDNA fragments generated by restriction digest can be analyzed, e.g., on an array, an array of indexing linkers (see, e.g., U.S. Pat. No. 5,508,169). If the hairpin primer, polymerase extended product, or amplified products is labeled with a capture or anchoring moiety, e.g., a biotin group, then it is possible to render the dsDNA fragments generated by the restriction digest single stranded, by thermal denaturation following the addition of capture or anchoring moiety reactive, streptavidin-labeled, substrates, e.g., magnetic beads or a solid support. Alternatively, the dsDNA fragments can be rendered single stranded by denaturation or by the action of an exonuclease. The single-stranded DNA fragments can be analyzed on an array of capture probes, using, e.g., fluorescent detection methodology.

In other embodiments, the captured DNA fragments are analyzed using mass spectrometry.

In other embodiments, the single-stranded DNA fragment mixture is applied to a multiplicity of wells, each containing a single RCA vector, (e.g., see U.S. Pat. No. 5,714,320). Rolling circle amplification is performed as taught by methods in the art, and the RCA products are analyzed using mass spectrometry following fragmentation, where the amplification of specific RCA vectors is determined by differences in molecular weight of the RCA product fragments. Likewise, the linear products generated by type IIs enzyme cleavage may be circularized using a single positioning oligonucleotide. The circular molecules can serve as template in a rolling circle replication mechanism.

The second step of the two step observational method determines the second subsequence. The second subsequence may be determined according to any procedure. A less preferred method involves the use of phasing primers. A plurality of PCR reactions are performed using a plurality of phasing primers. Production of PCR product then signifies the presence of additional phasing nucleotides recognized by a particular phasing PCR primer, and the second subsequence is constructed from the phasing nucleotides so recognized.

However, it is preferable to use a procedure that recognizes all the second subsequences in a simultaneous, parallel and quantitative manner. The preferred observational method of this invention uses a positional array for this purpose. The positional arrays of this invention a simple, high throughput device for simultaneous separation and detection of polymerase extended sequences and amplified fragments. In one aspect, the positional array contains all oligomers of a given length, such as, 4-mers, 5-mers, 6-mers, and so on. Using hybridization, ligation and polymerase extension, the array is capable of recognizing in parallel all second subsequences of that length in a single hybridization. At the same time, the positional array is also capable of comparing the quantitative presence of a subsequence in two or more sample, when the fragments of each sample are labeled with a unique tag.

In one aspect, this invention features a positional array containing capture probes wherein each capture probe is located at a predesignated location on the array. Further, each capture probe comprises a core region which is same in all the capture probes of the array and a variable region which is unique and not repeated in any other probe in the array. The size of the variable region of capture probes determines the total size of the array. In general, the size of an array wherein the capture probe comprises a variable region of N nucleotides is $4^N$ elements. For instance, a variable region of 4 nucleotides specifies an array of 4 raised to the power 4, or 256 elements in the array, a variable region of 5 bases specifies 4 raised to the power 5 or 1024, a 6-mer variable region specifies an array of 4096 elements, and so on. In preferred embodiments, the capture probes are anchored on a surface.

Figure 8:
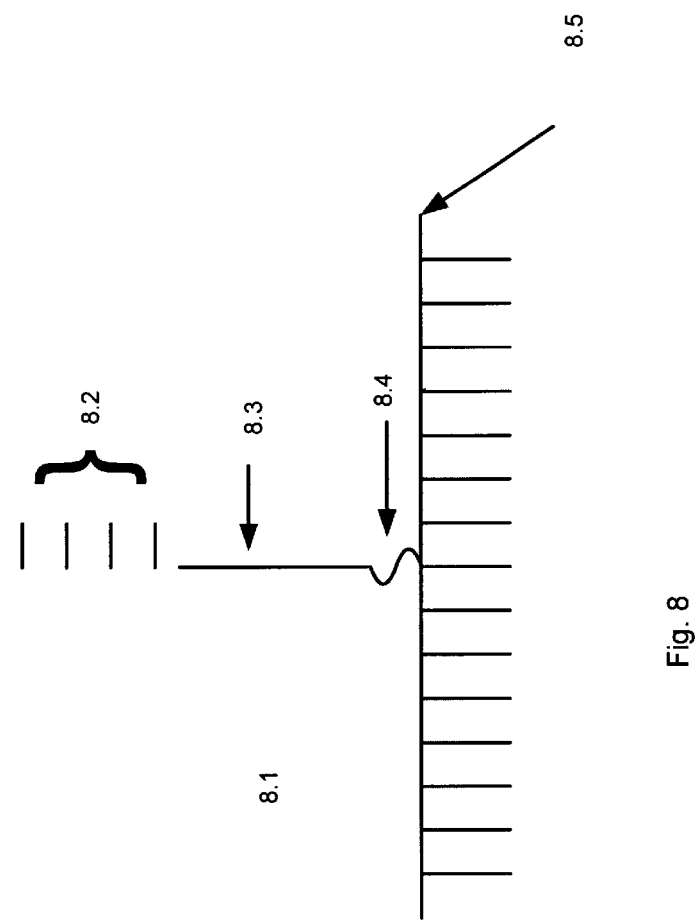
FIGS. 8 & 9 are drawings showing the structure of an array element of a positional array and hybridization of the cleavage product to the capture probe. The hairpin primer region, 2.1 is appropriately hybridized to the constant region 8.3 of capture robe.
Figure 9:
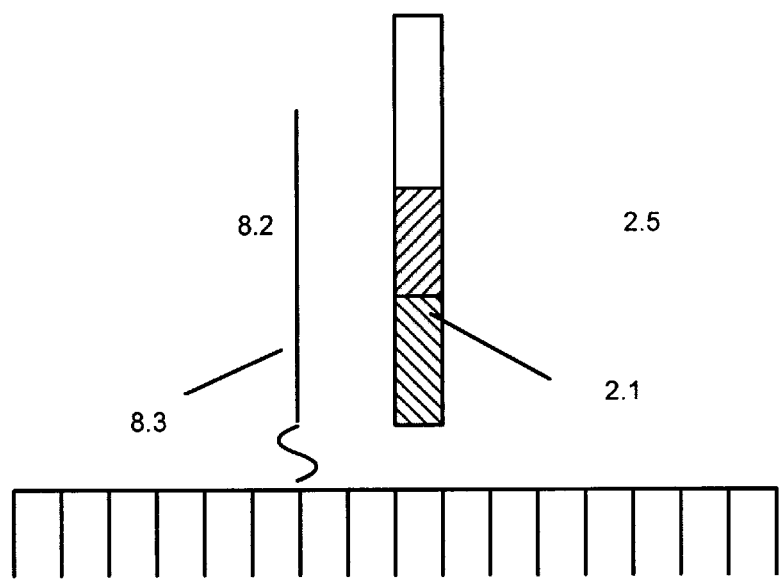

In more detail, the structure of a capture probe is described in relation to FIG. 8. The capture probe, 8.1, comprises a substantially linear structure having several regions of internal function and structure. In general, it comprises a constant region 8.3, and a variable region 8.2, a linker region, 8.4, and optionally, a spacer region. One or more of these regions can be nucleotide polymers, and the others can be either nucleotide polymers or other polymers or monomers of alternative structure. Region 8.2 is one that participates directly in the recognition of the second subsequences. As such, the length of region 8.2 is the same as the length in nucleotides of the second subsequence.

The length and sequence of the capture probe vary according to the application. The preferred methods of this invention generate a plurality of polymerase extended products from a nucleic acid sample wherein each of the fragments comprising the polymerase extended products contains the hairpin primer sequence inserted between the first and second subsequences, which is the same in any subset of fragments in a sample. As a consequence, all the fragments comprising a subset of polymerase extended products contain a recognizable sequence (the hairpin primer sequences or part thereof) but which recognizable sequences are absent from the original target sequences. The unique structure of the polymerase extended products (and the amplified sequences derived from the polymerase extended products) provides additional stability required for stringent hybridization to capture probes for the determination of the second subsequences on a positional array. Accordingly, the capture probe recognizes not only the second subsequence but also the regions of the hairpin (or its complement) that are located adjacent to the second subsequences in the polymerase extended products and amplified sequences. These aspects are described in detail in the applications outlined below.

Figure 10:
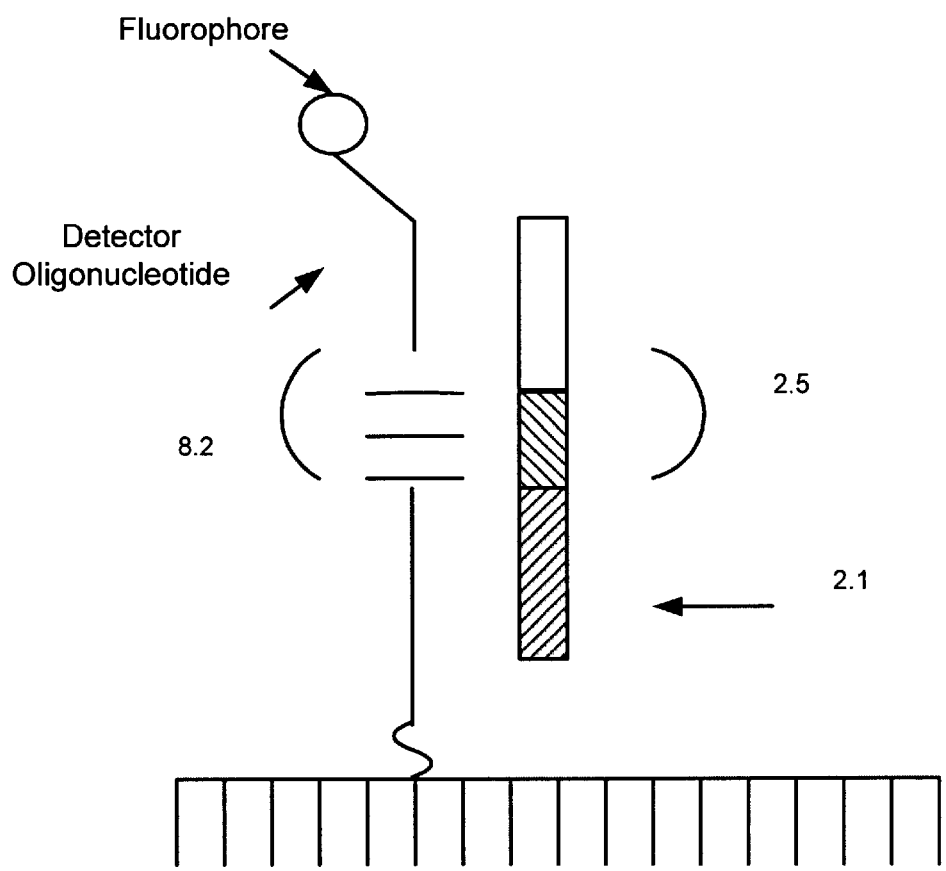
FIG. 10 is a schematic drawing of hybridization of a capture probe of the array to the polymerase extended product in the presence of a detector oligonucleotide. Detector oligonucleotide shown has covalently linked fluorophore.

In one application, second subsequences are determined by hybridizing polymerase extended products to the positional array. In one embodiment, the positional array contains capture elements that are anchored to the surface, 8.5, by their 5 ends. A plurality of array elements are present in the array wherein each element is positionally distinguishable from other elements of the array and contains a single species of capture probes, each capture probe containing a unique variable region not repeated in any other element in the array and a constant region that is common to most or all of the elements of the array. As shown in FIG. 10, the constant region of capture probes is complementary and hybridizable to the 5' ends of the polymerase extended products or single stranded fragments derived from the amplified sequences. The variable regions interrogate the second subsequences, which are located adjacent to the hairpin primer sequence in the polymerase extended products, thereby separating the fragments by hybridization. In a preferred embodiment, a detector oligonucleotide also hybridizes to the polymerase extended and/or amplified product and abuts the end of the capture probe thereby enhancing the specificity of the hybridization. The detector oligonucleotide can be one of a specific sequence, such as a gene-specific or locus specific oligonucleotide. Alternately, the detector oligonucleotide can be any sequence that enhances the hybridization, including one or more species of randomly selected oligonucleotides, such as a random hexamer. In preferred embodiments, the detector oligonucleotide is a specific sequence. A plurality of detector oligonucleotides can be employed for simultaneous determination of a plurality of second subsequences. In preferred embodiments, the genetic event is located within the second subsequence. The preferred methods of this invention detect sequence variations in nucleic acids by generating signals at different elements of the array for each variant. For example, consider the 5-mer subsequence, ACGTA, for which a sequence variant ACcTA exists, as shown in FIG. 10. In this example, the variant base is located in the third position of the subsequence, wherein 'G' is replaced by 'c'. Hybridization of polymerase extended fragments containing the two variant subsequences produces two signals, one for each variant second subsequence. Since the capture probes that produce perfect duplexes for each of the variants in the subsample are positionally distinguishable, two independent signals are generated, one at each separate location in the array. This must be contrasted with methods described in the art (Barany et al, U.S.

Pat. No. 6,027,889; Yager et al, U.S. Pat. No. 6,025,139) wherein the two variant signals are generated at the same element of the array and are observed as distinguishable labels. These methods are hereby incorporated by reference. In a somewhat similar approach, Nikiforov et al. (U.S. Pat. No. 5,952,174) describe a method for determining the identity of a nucleotide at a preselected site in a nucleic acid molecule involving a single base extension by a polymerase followed by ligation. This method combines the specificity of a polymerase with that of a ligase in determining the identity of the nucleotide in a target. However, the approach does not circumvent the need for a specific capture molecule for each target species, thereby decreasing throughput and cost efficiency. Further, these applications are limited to determination of genetic events at nucleotides that are positionally constrained, i.e., at or adjacent to the genetic event. Other methods described in the art include for positional include U.S. Pat. No. 5,503,980 and PCT\WO9928505, herein specifically incorporated by reference, wherein single strand ends generated at the termini of partially single stranded molecules are ligated to capture probes. The methods taught by PCT\WO9928505 identify additional subsequences located adjacent to a primary nucleotide subsequence wherein a primary nucleotide subsequence is the recognition site of a restriction endonuclease site in nucleic acids. Thus, the approach is limited by the positional constraints placed on the location of the additional subsequences. In U.S. Pat. No. 5,503,980, a nucleic acid fragment that is at least partially single stranded is ligated to a capture probe, wherein the terminal single stranded nucleotides of the partially single stranded capture probes are hybridizable to the ends of capture probes. However, the approach is difficult to practice as a few terminal bases only determine duplex yield and strength of the hybrids. In U.S. Pat. No. 4,988,617 (herein incorporated by reference), two probes selected to be substantially complementary to the selected region of the DNA test substance and directly adjacent to each other in a head to tail relationship are ligated by hybridization to a target nucleic acid, wherein at least one of the probes is labeled with a detectable moiety. The first target probe capable of annealing to a first portion of the test substance has a nucleotide end region complementary to the normal or mutated nucleotide at the mutation position, i.e. the target nucleotide position. An adjacent olignucleotide probe for annealing to a second portion of the test substance contiguous to the first portion. The target and adjacent probes are complementary to two contiguous predetermined sequences of the test substance.

In contrast to methods described in the art, the methods of the present invention are independent of where the genetic event is located, so long as they are located within the first or second subsequence. The first subsequence is determined at the time of hybridization of the hairpin primer to the partially single stranded nucleic acid fragment in the subsample. Further, the present invention requires a single target specific primer, either the capture probe or detector oligonucleotide. Where ligation is employed for detection, the other probe is a single species of detector probe, which is same for all subsets in a fragment subsample hybridizing to the capture probes of the array, wherein the readout is positional. Thus, the present invention provides a convenient and cost-effective method for identifying subsets of nucleotides in a nucleic acid fragment. Further, the constant regions of capture probes of this invention hybridize to a recognizable sequence in the fragments of this invention, thereby providing additional duplex stability to the hybridization structures. The variant bases of the capture probes then interrogate the second subsequences and provide a positional signal. If a variant base is present in more than one fragments of the subsample, a signal for each of the subsequences will nevertheless be generated, but the location of the signal at any one or other element of the array will determine the subsequence, thereby simultaneously identifying the location as well as the identity of the variant base. According to this invention, to determine the complete sequence of a nucleic acid target, the set of probes need not contain every possible combination of nucleotides of the random sequence to be encompassed by the method of this invention. Methods taught by U.S. Pat. No. 5,002,867 (hereby incorporated by reference) wherein degenerate bases are used in different probe subsets to decrease the total number of probes required for determination of nucleotides in a target may be advantageously employed.

Figure 11:
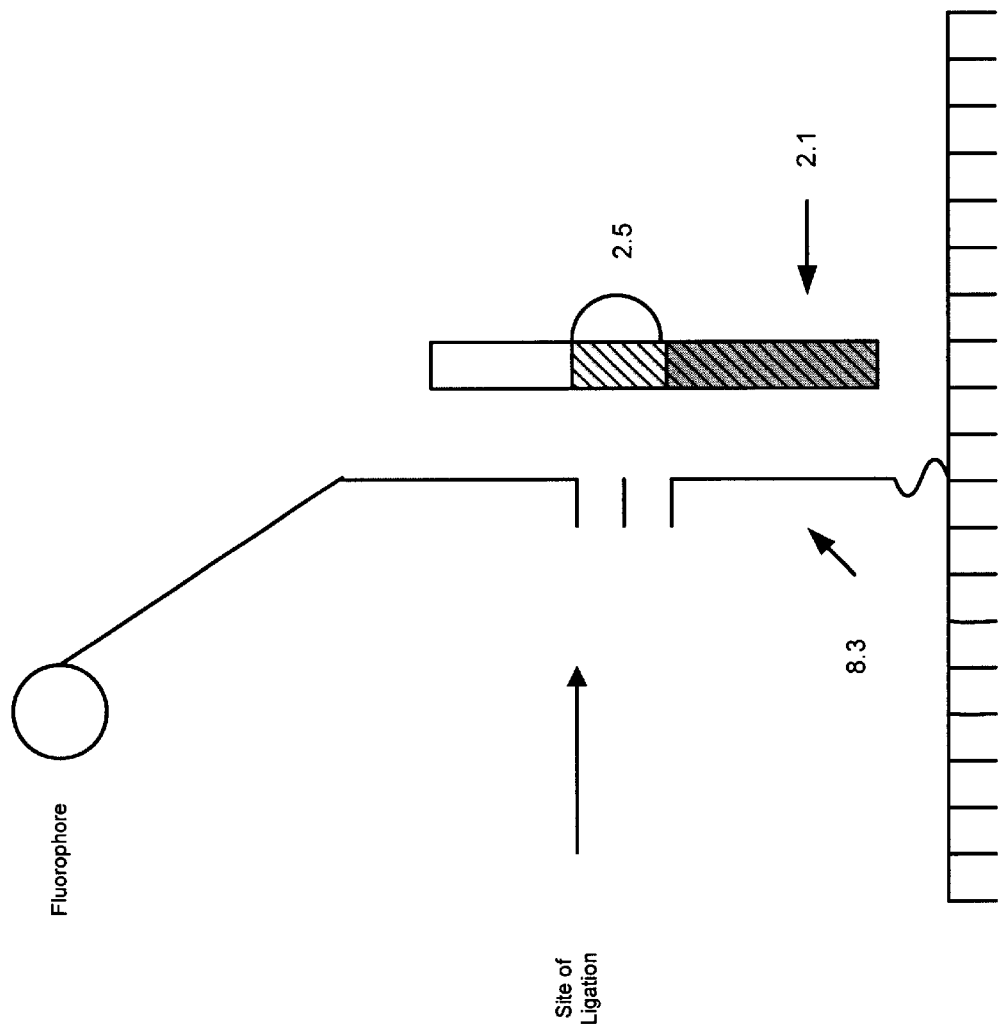
FIG. 11 is a schematic drawing of hybridization of a capture probe of the array to the polymerase extended product in the presence of a detector oligonucleotide wherein the detector oligonucleotide is ligated to the capture probe.
Figure 12:
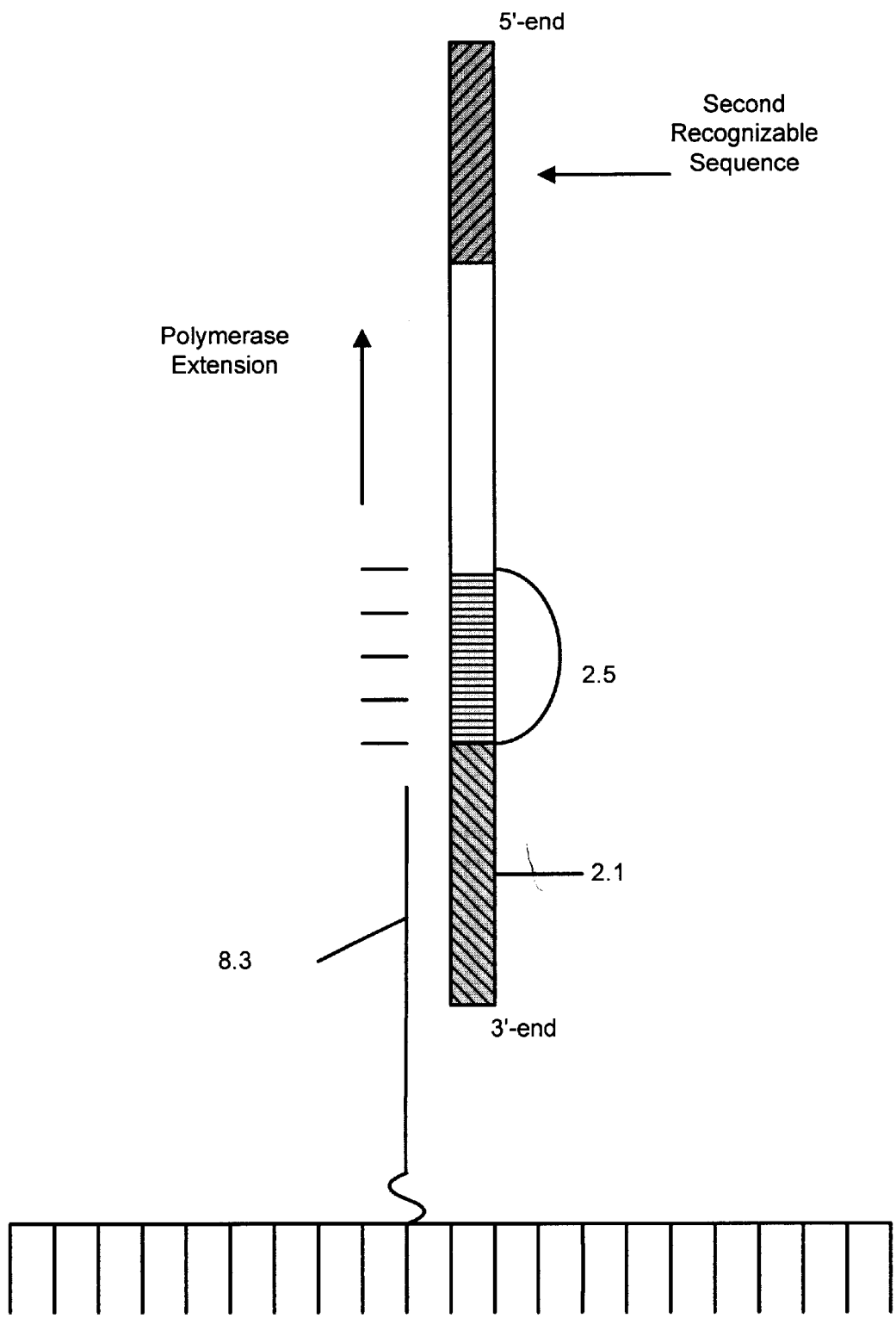
FIG. 12 is a schematic drawing of a capture probe of the array to the polymerase extended product wherein the capture probe is a substrate for extension by a polymerase using the polymerase extended product as template.

The preferred methods of this invention employ enzymatic methods to enhance hybridization, as a detection means and for amplifying the detection signals. For example, as shown in FIG. 11, the detector oligonucleotide can be ligated to the capture probe, such ligation generating a signal. In preferred embodiments, the detector oligonucleotide contains a detectable label. For detection, any known label for proteins, peptides or nucleic acids may be used in accordance with the present invention. Such labels include radioactive tags, enzymes, fluorescent tags, colorimetric tags and amplifiable tags, such as an RCA primer. Examples of fluorophores include but are not limited to Cy3, Alexa dyes, Cy5, Fluorescein, Rhodamine, etc. Examples of haptens include but are not limited to biotin, digoxigenin, etc. Haptens can be detected using an enzyme conjugated antihapten antibody, followed by performing the enzymatic reaction that generates an observable signal localized in the element of the array.

In another application, an array of capture probes is prepared wherein the variant region is located at the 3' terminus and probes are immobilized from their 5' ends. Following denaturation, one strand of amplified fragments is captured on the array by hybridization. Detection can be performed by a variety of methods. In one case, detector oligonucleotides can be hybridized and enhanced by ligation. Again, the presence of a variant base in the second subsequences are interrogated by the variant regions of capture probes and generate signals at distinct elements of the array. The preferred linking agent is a ligase, preferably T4 DNA ligase, using well known procedures (Maniatis, T. in Molecular Cloning, Cold Spring Harbor Laboratory (1982)). T4 DNA ligase may also be used when the substance is RNA (The Enzymes, Vol. 15 (1982) by Engler M. J. and Richardson C. C., p. 16–17. Methods in Enzymology, Vol. 68 (1979) Higgins N. P. and Cozzarelli N. R. p. 54–56). Other DNA ligases may also be used, such as those derived from thermophilic organisms, thus permitting ligation at higher temperatures allowing the use of longer probes (with increased specificity) which could be annealed and ligated simultaneously under the higher temperatures normally associated with annealing such probes. The linking agent may also be a chemical agent that will cause the probes to link unless there is a nucleotide base pair mismatching at the target nucleotide position.

In another case, the capture probes can be extended by a polymerase in presence of deoxynucleotide triphosphates, at least one of which is labeled with a detectable moiety. In another case, the capture probe can be extended along the length of the amplified fragment, resulting in copying of the second recognizable sequence present at the 5' terminus of amplified sequences. After washing to remove the amplified fragment, the copied second recognizable sequence can serve as a primer for rolling amplification. This is performed by annealing a circle that contains a region identical to the sequence of the second recognizable sequence and extending with a polymerase in the presence of deoxynucleotide triphosphates.

In another aspect, this invention features an array comprising capture probes of particular sequences of interest. A plurality of probes in the array hybridize to a plurality of target fragments providing a hybridization structure. In this hybridization structure, the polymerase extended product is hybridized to a capture probe whose terminus is adjacent to a nucleotide of the second subsequence that, in turn, is adjacent to the hairpin sequence. Detection can be performed by any of the methods described above. Advantageously, a single detector oligonucleotide is needed whose sequence is complementary to the hairpin sequence contained in the fragment. The detector oligonucleotide hybridizes to the hybridized polymerase extended products and abuts the end of the capture probe, which can be ligated to the capture probe. Alternatively, the capture probe can be extended along the length of the hybridized polymerase extended product by one or more nucleotides.

Nucleic acid probes created by the method of the present invention are useful in a diagnostic aid to screen a biological sample, such as, for determining genetic variations of nucleic acid sequences in the samples. The set of nucleic acid probes and the target nucleic acid may comprise DNA, RNA, PNA, or other combination thereof, and may be derived from natural sources, recombinant sources, or be synthetically produced. Conditions for hybridization of nucleic acid targets to these probes have been described in *Nucleic Acid Hybridization: A Practical Approach* (B. D. Hames and S. J. Higgins, editors, IRL Press, 1985) and is hereby incorporated by reference.

Enzymes and Proteins

The various enzymes described herein are either commercially available or may be prepared by methods known in the art. These include restriction endonucleases (type II and type IIs enzymes), ligases, polymerases, exonucleases, and other DNA modifying enzymes. The enzymes described in this invention may also be employed for tagging nucleic acids, detection of signals, or as anchors.

Other suitable proteins that may be used in this invention are those that have affinity to or bind to DNA. These include, but are not limited to, single strand binding protein (SSB), recA or its homologues, mismatch detecting proteins of bacterial, viral or mammalian origin, or other proteins that associate with DNA.

The methods described herein are equally adaptable to the use of chemical entities that associate with or modify nucleic acids reversibly or permanently, such as pyrilium iodide, propidium iodide, ethidium bromide, TOTO, YOYO, Sybr Green, neocarzinostatin, cisplatin, bleomycin, etc.
Formats and Devices:

The methods described herein can be performed in single tubes, on surfaces such as glass, silica matrices, cellulose, nitrocellulose, nylon, or aluminium oxide membranes, acrylamide, polystyrene, polypropylene, vinyl acetate, polymethacrylate, polyethylene, polyethylene oxide, polycarbonates, polyesters, polypropylfumarates, polyglycollic acid, polyanhydrides, glycosaminoglycans, polyaminoacids, silicon rubber, agarose, latex, silicon dioxide, fluorocarbons, metal supports, teflon, plastic, or other supports known in the art.

The surfaces can have any form including, but not limited to, three-dimensional arrays such as, gel pad arrays, wells or microwells, porous structures such as channels, microchannels, beads or microparticles the preferred forms of the substrate include, glass, microtiter dishes, three dimensional acrylamide or agarose gel pad arrays, and porous membranes. The methods are equally adaptable to other forms of the substrate such as thin films, bottles, dishes, fibers, or shaped polymers.

Detection

Several methods of detection can be employed.
Fluorescent Labels:

In active labeling, DNA fragments generated by the methods of this invention are directly labeled during the DNA polymerization step by incorporation of a fluorescently labeled deoxynucleotide or hapten using any of the methods known to those skilled in the art. In passive labeling, the fragments are detected by hybridization to a labeled oligonucleotide, such as the detector oligonucleotide. Passive labeling oligonucleotides are labeled using fluorescence, haptens, or proteins using any of the methods known to those skilled in the art. In both labeling methods, the number of hybridized fragments are then quantitatively determined by determining the amount of label, such as fluorescent label present. This invention is equally adaptable to other forms of detection including, but not limited to, FRET, FRET-Quench, reversible interaction with proteins, redox labels, chromophoric substances, proteases and other proteins that effect cleavage reactions, calcium/calmodulin interactions, green fluorescent proteins, haptens or intercalating agents.

Positional Arrays

Suitable positional arrays include high and low density arrays on a two-dimensional or three-dimensional surface. Positional arrays include nucleic acid molecules, peptide nucleic acid molecules or high affinity binding molecules of known sequence attached to predefined locations on a surface. Arrays of this nature are described in numerous patents that are herein incorporated specifically by reference, (Cantor, U.S. Pat. No. 5,503,980, Southern, EP0373203 B1, and U.S. Pat. No. 5,700,637, Degau U.S. Pat. No. 5,508,169). The density of the array can range from a low density format, e.g., a microtiter plate, e.g. a 96- or 384-well microtiter plate, to a high density format, e.g., 1000 or higher elements/cm$^2$, as described in Fodor U.S. Pat. No. 5,445,934.

The invention will be further described in the following examples, which do not limit the scope of the invention described in the claims.

EXAMPLES

Example 1
Preparation of Subsamples

This example sets forth exemplary protocols for preparing subsamples of nucleic acid fragments such that all fragments in each subsample have selected first and second recognizable sequences, and are partially single stranded.

Numerous protocols for the isolation of genomic nucleic acid and mRNA populations from cells and tissues have been widely described in the art. Protocols for synthesis of double stranded cDNA (dscDNA) populations starting from the mRNAs have also been described. Any such appropriate protocols can be used to prepare nucleic acid samples from the tissues samples of interest.

A preferred protocol for subsample preparation from genomic nucleic acids or double stranded cDNA populations is described herein. Initially, the dsDNA sample is separated into several batches of from 100 ng to 5 µg each; the total number of subsamples being at least equal to the number of fragment subsamples. Each fragment subsample derives from the original nucleic acid but has a different second recognizable sequence. The method of generation of second recognizable sequences is now described by the following example.

RE Digestion:
1. Combine 1–5 µg of sample genomic DNA or dscDNA with 5 µl of 10×EcoRI buffer in a microcentrifuge tube and deionized water to 50 µl.
2. Mix and incubate tube at 37° C. for 2 min.
3. Add 2 µl of EcoRI enzyme (New England Biolabs, Beverly, Mass.).
4. Mix by tapping gently and spin briefly in a microcentrifuge.
5. Incubate at 37° C. for 1 hr.
6. Stop the reaction by incubating at 65° C. for 10 min.

Adapter Ligation:
A preferred linker oligonucleotide comprises:
5'-Phosphate-AATTGTAATACGACTCACTATAGGGC-OH-3' (SEQ ID NO: 1).
Preferred Adapter oligonucleotide is:
5'-OH-AAGCGCCCTATAGTGAGTCGTATTAC-3' (SED ID NO: 2)
Prepare linker-adapter mix by combining Inmole each of adapter (SEQ ID NO: 1) and linker (SEQ ID NO: 2) oligonucleotides in 50 µl of water. Heat to 95° C. for 5 min and allow to cool slowly to room temperature. Store at −20° C.

To the RE digest from above, add:
1. 2 µl of linker-adapter mix, and 2 µl of T4 DNA Ligase (New England Biolabs).
2. Incubate at 16° C. for 4 hours.
3. Stop the reaction by incubating at 65° C. for 10 min.

Other examples of type II REs that can be used are commercially available from New England Biolabs, Stratagene (La Jolla, Calif.), etc. Preferably, those REs that have a six-base recognition site and leave at least a 4 base overhang are employed.

Example 2
Generation of a Subsample Containing Partially Single Stranded Fragments by Digestion With an Exonuclease This example describes a preferred method for converting the RE digested and adapter ligated fragments from Example 1 into partially single stranded fragments by digesting the fragments with an exonuclease. A preferred exonuclease is Exonuclease III (Stratagene).

1. Combine the following reagents in a microcentrifuge tube:
   2 µl of reaction products from Example 1
   10 µl of 10×ExoIII buffer (final concentration: 50 mM Tris-HCl, 5 mM
   MgCl2
   87.5 µl water.
2. Mix and incubate at 37° C. for 3 min.
3. Add 0.5 µl (50 units) of ExoIII (Stratagene).
4. Mix and incubate at 37° C.
5. At intervals of 1 min., transfer 5 µl aliquots into a separate tube containing 2 µl of 20 mM EDTA. Mix immediately.
6. Collect as many aliquots as necessary.
7. Stop the reaction by incubating at 65° C. for 10 min.
8. Add 44 µl of water to each aliquot.
9. Storeat −20° C.

Example 3
Generation of a Subsample Containing Partially Single Stranded Fragments by Hybridization of an Anchoring Oligonucleotide This example describes a preferred method for converting the RE digested and adapter ligated fragments from Example 1 into partially single stranded fragments by hybridization of an anchoring oligonucleotide. A preferred anchoring oligonucleotide comprises the sequence 5' OH-CTCAAAGAGGCCAAGGCAGG-3' (SEQ ID NO: 3).

1. Mix the following reagents in a microcentrifuge tube:
   2 µl of reaction products from Example 1
   2 µl of 1 pmol/µl anchoring oligonucleotide (SEQ ID NO: 3)
   46 µl water
2. Heat the tube at 95° C. for 3 min. Quick chill on ice.
3. Store at −20° C.

Example 4
Hybridizing Hairpin Primer to Partially Single Stranded Fragrnents and Polymerase Extension A preferred hairpin probe comprises the sequence, 5'-phosphate-CAGATCGTCGTTCACTACTGCACGGATGCACGCACT-3' (SEQ ID NO: 4). Prepare a solution of 1 pmol/µl hairpin primer. Incubate at 50° C. for 10 min. Allow to cool slowly to room temperature.

1. In a microcentrifuge tube, combine,
   5 µl of reaction products from Examples 2 or 3
   1 µl hairpin solution
   2 µl 10×Klenow buffer (New England Biolabs)
   11 µl water.
2. Incubate at 30° C. for 30 min
3. Add 1 µl 1 mM dNTP mix
4. Mix and incubate at 37° C. for 2 min.
5. Add 1 µl Klenow fragment, exo- (New England Biolabs)
6. Incubate at 37° C. for 30 min.
7. Stop the reaction by incubating at 65° C. for 10 min.

Example 5

Preferred primers for PCR are, P1, 5'-CACTACTGCACGGATGCACG-3' (SEQ ID NO: 5); and P2, 5'-OH-AAGCGCCCTATAGTGAGTCGTATTAC-3' (SEQ ID NO: 2).

1. In a PCR tube, mix the following components:
   2 µl products from step 7 of example 4
   20 pmole P1
   20 pmole P2
   5 µl 10×PCR buffer (500 mM Tris-HCL, pH9.15;n 160 mM (NH4)S04,
   20 mM MgCl2).
   2 µl 10 mM dNTP (equimolar mixture)
   water to 50 µl.
2. Mix solutions by tapping or inverting the tubes (do not vortex).
3. Place tubes in a thermal cycler and perform the following thermal cycling protocol. Preferably 20 cycles are performed.

96° C. for 30 sec.
57° C. for 1 min
72° C. for 1 min

4. After the cycling program is finished, heat the tube at 75° C. for 5 min.
5. Place finished reactions in freezer or proceed to next step.

Example 6

Amplifying Polymerase Extended Products by Rolling Circle Amplification

1. In a microcentrifuge tube, mix the following components:
   1 μl products from step 7 of example 4
   1 pmole primer P2
   2 μl NEBuffer4 (New England Biolabs)
   1 μl 1 mM dNTP mix
   4 μl water
2. Mix, spin briefly in a microcentrifuge.
3. Add 1 μl Klenow enzyme.
4. Incubate at 37° C. for 30 min.
5. Stop the reaction by incubating at 65° C. for 10 min.

The products from the above step are next cleaved by incubation with FokI, a type IIs restriction endonuclease.

6. Add 1 μl FokI (New England Biolabs) to tube from step 5.
7. Incubate at 37° C. for 30 min.
8. Stop the reaction by incubating at 65° C. for 10 min.

In the next step, the products from FoKI digestion are circularized by ligation in presence of a positioning oligonucleotide. The sequence of a preferred positioning oligonucleotide, P3, is 5'-CGACGATCTGAGGTGCGTGC-3' (SEQ ID NO: 6). The preferred sequence of the RCA primer, P4 is, 5'AAGCTGCATCCGTGCAGTAGTGAAC-3' (SEQ ID NO: 7). The preferred method of circularizing digestion products from step 8 is now described.

9. Combine 2 μl of product from step 8 with 1 μl of 1 pmol/μl P3 oligonucleotide, in 20 μl of a buffer containing 20 mM Tris-HCl, 0.01% Triton X-100, 10 mM MgCl2, 0.5 mM AND, pH 8.3.
10. Heat the tube at 95° C. for 3 min. Allow to cool slowly to 65° C.
11. Add 25 units of Ampligase (Epicentre Technologies, Madison Wis.).
12. Incubate at 65° C. for 1 hour.
13. Add 1 μl of 0.75 M KCl, 1 μl dNTP mix (750 μM each dNTP), 3 μM P4, DMSO to final concentration of 1.5%, 10 μM T4 gene-32 protein (Amersham Life Sciences, Piscataway, N.J.) and 10 units Vent (exo-) DNA polymerase (New England Biolabs) in a final volume of 50 μl.
14. Heat the tube to 90° C. for 5 min and incubate at 60° C. for 1 hour.

Example 7

Designing and Preparing Capture Probes

A preferred surface for the preparation of positional arrays is glass. The array preparation steps include derivatizing the surface, designing and preparing probes, and depositing probes on the surface. Methods of derivatizing glass surfaces have been described in the art (Guo et al, Nucleic Acids Res (1994) 22:5456–65). This example describes a preferred method of designing probes.

As dia grammed in FIG. 8, a capture probe is a substantially linear structure comprising of a linker, 8.4, a constant region, 8.1, and a variable region 8.2. Optionally, one or more spacer regions may be present.

The preferred structure of an exemplary capture probe is now described. It comprises an attachment region, such as a chemical moiety reactive with the particular surface chemistry employed. For instance, when the chemistry described by Guo et al is used for coating glass slides, probe molecules contain a terminal —NH2 group that mediates the covalent binding of the oligonucleotide to the surface. Other surface chemistries have been described in the art that require probe molecules to contain terminal —SH, -phosphorothioate, or other chemical moieties. Accordingly, the probe molecules will be synthesized that contain the particular terminal reactive moiety preferred by the chemistry. A preferred attachment moiety is —NH2 group.

Probes contain a spacer region. Typically a spacer is an aliphatic carbon chain, such as C6, C12 or C18, that are commercially available (Glenn Research) and are incorporated during the synthesis of oligonucleotides by synthetic oligonucleotide suppliers (i.e., BioSynthesis, Lewisville Tex.). Other forms of spacers include, nucleotide spacers, such as, homopolymers of T or A nucleotides, containing 15–50 repeats.

The spacer region is followed by a constant region, 8.1, that is common to all the capture probes comprising the set of probes. The constant region can be of any sequence, but is preferably one that is not likely to be present in the sample nucleic acid. Further, in some applications, the constant region has a sequence that is complementary to the hairpin sequence, or is the same as the hairpin sequence. Accordingly, preferred sequences of the constant regions are, 8.1a, 5'-CGTGCATCCGTGCAGTCGTG-3' (SEQ ID NO: 8), or 8.1b, 5'-CACTACTGCACGGATGCACG-3' (SEQ ID NO: 9).

The terminal portions of capture probes contain a variable region, that is, one that is not repeated in any other probe of the set. Probes are then numbered, such as, CP1 constitutes a probe with the terminal sequence AAAA, CP2 constitutes probe with AAAT, CP3 with AAAC, CP4 with AAAG, CP65 with TAAA, CP80 for probe TAAG and so on. In this manner, probes of the positional array are assigned an identity, which facilitates handling during their deposition onto arrays and in their identification on the array. Likewise, a 5-mer probe set will have numbers from 1 through 1024, a 6-mer from 1 through 4096, and so on.

Accordingly, the preferred structure of a capture probe 1 in a positional array of probes is 3'-NH2-C18-(T)15-GTGCTGACGTGCCTACGTGCAAAA-5' (SEQ ID NO: 10). The sequences of the other probes in the positional array are easily derived from the foregoing discussion.

Example 8

Depositing the Probes on a Glass Surface

The preferred methods for array generation are now described. A positional array contains a number of elements equal to all possible n-mers for a capture probe wherein the number of variable nucleotides have a value of n. a preferred value of n is 4 nucleotides, wherein the total array size is 256 elements. Larger arrays where the values of n are 5 or 6 are also preferred, in which case the total array sizes are alt least 1024 or 4096, respectively. Typically, arrays also contain other probes, accessory probes such as, scaling control probes, data normalization control probes, and marker probes that help in determining the extent of hybridization and data analysis and interpretation. Arrays can also contain a subset of the n-mers or other capture probes of interest.

For array generation, a solution of each capture probe is prepared. A preferred solvent for capture probes is 10 mM Tris-HCl, 10 mM NaCl, pH 8.0 or equivalent buffer. The preferred concentration of capture probes is 1 to 100 µM. Solutions of capture probes are placed into the wells of a multiwell plate, in 96- or 384-well format in an ordered manner. The manner in which capture probes are placed into the multiwell plate depends upon the method used for arraying the probes onto a derivatized glass slide. For instance, CP1 is placed into well A1 of a 96-well plate, CP2 into well A2, CP3 into well A3, and so on until all the wells are filled. A second 96-well plate is then used, wherein CP97 is placed in well A1, Cp98 into well A2, and so on. Thus, three 96-well plates are needed to dispense all the 256 capture probes, the remaining 32 wells may be left empty or used for dispensing the accessory probes. Alternatively, a single 384-well plate is used. Aliquots of probes are transferred from the microwell plate to predesignated spots on the glass slide using a mechanical robot containing a pin that aspirates the probe sample by dipping into the sample. A preferred arraying robot is the OmniGrid (GeneMachines, San Carlos, Calif.). A single dip of the pin into a microwell containing a single species of probes produces a plurality of spots on one or more glass slides. A washing step is included before the pin dips into another microwell. A plurality of aspiration and dispensing steps result in transferring all the probes in the plate to predesignated locations on the glass slides. A map relating the identity of probes in microwells to their location on the glass slides is thereby created. In preferred methods, each element of the array is 150–200 µm in diameter and different spots have a spacing of at least 250 µm. Printed microarrays are then incubated in a humid chamber for 2–16 hours to promote covalent association of probes to the glass surface.

Prior to hybridization, microarrays are deactivated and blocked. Preferred methods of deactivating amino silane-PDITC slides have been described in the art and involves the use of a primary amine, such as glycine, ethanolamine or their derivatives, and blocking with proteins, single stranded DNA or non fat dry milk.

Example 9
Hybridization Protocols

Microarrays are hybridized with polymerase extended products or heat denatured amplified products (hereinafter termed "products") in the presence of detector oligonucleotides. A preferred sequence of a detector oligonucleotide is, 5'-fluorophore-GAGCCCAGGAGTCAAGACC-3' (SEQ ID NO: 11). Preferred fluorophore is Cy3 (Amersham). The preferred method for hybridization of the microarrays is now described.

The hybridization solution contains; 2–5 µl polymerase extended products or amplified products, in 2z SSC. 0.05% Tween-20, 10 mM sodium phosphate buffer, pH 7.0 and 1 pmol of detector oligonucleotide. The hybridization mix is heated to 80° C. for 3 min and 10 µl is pipetted onto the array. A glass coverslip is placed so as to cover the array, being careful to remove air bubbles by tapping gently. The microarrays are incubated for 2–16 hours in a humidified chamber at 50° C.

Following hybridization, the coverslips are removed and microarrays are washed with three changes of 2×SSC/0.05% tween-20 for 5 min each, rinsed in 2×SSC and dried by spinning in a table top centrifuge. The slides are then scanned in a laser scanner, such as ScanArray5000 (GSI Lumonics, Watertown, Mass.) or equivalent, with the instruments settings selected for detection of the appropriate fluorophore.

Example 10
Detection Method Using Hybridization/ligation

Preferred methods of this invention include increasing the specificity of hybridization by ligating detector oligonucleotides to the terminus of capture probes. As mentioned in the detailed description, polymerase extended or amplified products and the detector oligonucleotides together form a hybridization structure wherein the detector oligonucleotide hybridized to the polymerase extended products abuts the end of the capture probe.

A preferred ligase enzyme is Ampligase. The ligation method is now described. In 2-step ligation, the fragment subsample is hybridized to arrays as mentioned in Example 9. After washing, the microarrays are incubated under coverslip with 10 µl of a solution containing, 20 mM Tris-HCl, 0.01% Triton X-100, 10 mM MgCl2, 0.5 mM NAD, pH 8.3, and 25 units of AmpLigase. Microarrays are incubated at 60° C. in a humid chamber for 1–16 hours. The microarrays are then washed as described for hybridization, except that the washing steps are performed at 90° C. so as to wash away any unligated hybridized structures.

The microarrays are then scanned as described.

In one step ligation, microarrays are incubated with 10 µl of a solution containing 20 µM Tris-HCl, 0.01% Triton X-100, 10 mM MgCl2, 0.5 mM AND, pH 8.3, 2–5 µl products and 25 units of AmpLigase for 1–16 hours at 60° C. microarrays are washed and scanned as described.

Example 11
Detection Method Using Polymerase Extension

The polymerase extension mix contains

1×polymerase buffer

1 µM each of dATP, dGTP and TTP

2–5 µl products 200 nM fluorophore labeled dCTP 25 units Vent exo- polymerase water to 10 µl.

The polymerase mix is pipetted onto the array, covered with a coverslip and incubated in a humid chamber at 60° C. for 1–16 hours. Microarrays are washed as described in example 10, and scanned.

What is claimed is:

1. A method for identifying and quantifying a nucleic acid in a sample of nucleic acids, the method comprising:

(a) providing at least one of a plurality of subsequence sets present in the sample of nucleic acids, wherein each subsequence set comprises:
a first recognizable sequence;
a composite subsequence of nucleotides comprising a first subsequence and a second subsequence; and
a second recognizable sequence, such that:
the composite subsequence is adjacent to the first recognizable sequence and non adjacent to the second recognizable sequence;
the second recognizable sequence comprises a recognition site of a restriction endonuclease that cuts nucleic acids within the recognition site; and
the subsequence set is observed to be present in the sample of nucleic acids;

(b) digesting nucleic acids from the sample so as to provide at least one subsample of partially single-stranded nucleic acid fragments;

(c) determining the sequences of composite sequences located in the single-stranded portion of said partially single-stranded nucleic acid fragments in each subsample, by:
annealing the nucleic acid fragments with at least one species of a polynucleotide primer having a hairpin structure, wherein the hairpin primer comprises, from 5'- to 3'-direction:
a nucleic acid contacting region hybridizable to a first subsequence from at least one nucleic acid fragment from the subsample;
a first stem region; a loop region; a second stem region that is complementary to the first stem region; and
a second nucleic acid contacting region hybridizable to a second subsequence of the nucleic acid fragment from the subsample, to obtain a plurality of primed nucleic acid fragments wherein the first and second stem regions remain double-stranded after hybridization;
incubating the primed nucleic acid fragments with a DNA polymerase and at least two deoxyribonucleotide triphosphates under conditions promoting polymerization of nucleotides at the 3'-terminus of the hairpin primer, so as to produce polymerase extended products and to determine the nucleotide sequence of the extended products;

(d) detecting the polymerase extended products;

(e) quantifying the polymerase extended products using any standard quantification method including fluorescent labeling, hapten labeling, and hybridization to similarly labeled complementary oligonucleotides; and (f) searching a database of nucleic acid sequences in order to locate database sequences having the observed subsequence sets, the database nucleic acid sequences comprising nucleic acid sequences that might be present in the sample, and identifying the located database sequences as sequences of the subsequence sets nucleic acids present in the sample.

2. The method of claim 1, wherein the composite subsequence comprises a first subsequence adjacent to a second subsequence, such that:

the first subsequence may be contiguous to or is spaced apart from the second subsequence by at least one nucleotide having the same sequence and length in all subsets;

the second subsequence is spaced apart from the first recognizable sequence by a length of nucleotides at least equal to the number of nucleotides in the first subsequence; and the second recognizable sequence is spaced apart from the composite subsequence by a variable number of nucleotides.

3. The method of claim 1, further comprising:

hybridizing the digested nucleic acids with adapter nucleic acids, the adapter nucleic acids being partially double stranded, each adapter nucleic acid being complementary to an end of the resulting restriction enzyme digested nucleic acid;

ligating the hybridized nucleic acids and adapter nucleic acids;

denaturing the nucleic acid fragments to produce single stranded fragments; and incubating the single stranded fragments with at least one species of anchoring oligonucleotide under conditions that promote hybridization of the anchoring oligonucleotide with the single stranded fragments, wherein the anchoring oligonucleotide is a hybridizing primer that hybridizes adjacent to the composite subsequence.

4. A method of identifying a nucleic acid in a sample of nucleic acids, the method comprising:

(a) providing at least one of a plurality of subsequence sets present in the sample of nucleic acids, wherein each subsequence set comprises:

first and second recognizable sequences wherein the second recognizable sequence comprises a recognition site of a restriction endonuclease;

at least one composite subsequence adjacent to the first recognizable sequence and non-adjacent to the second recognizable sequence;

(b) digesting nucleic acids derived from the sample with an exonuclease so as to provide at least one subsample of partially single-stranded nucleic acid fragments derived from the nucleic acids in the sample;

(c) determining the sequences of composite subsequences located in the single-stranded portion of the partially single-stranded fragments in each subsample by:
annealing the nucleic acid fragments with at least one species of polynucleotide primer having a hairpin structure, wherein the hairpin primer comprises, from 5'-to 3'-direction:

a first nucleic acid contacting region hybridizable to a first subsequence from at least one nucleic acid fragment from the subsample;

a first stem region; a loop region; a second stem region that is complementary to the first stem region; and a second nucleic acid contacting region hybridizable to a second subsequence of the at least one nucleic acid fragment from the subsample, to obtain a plurality of primed nucleic acid fragments wherein the first and second stem regions remain double-stranded after hybridization; and incubating the primed nucleic acid fragments with a DNA polymerase and at least two deoxyribonucleotide triphosphates under conditions promoting polymerization of nucleotides at the 3'-terminus of the hairpin primer; and (d) identifying polymerase extended products.

5. The method of claim 4, wherein digesting further comprises:

digesting the sample with at least one endonuclease whose recognition site has the second recognizable sequence; and hybridizing the digested nucleic acids with adapter nucleic acids, the adapter nucleic acids being partially double stranded, each adapter nucleic acid being complementary to an end of the digested nucleic acid;

ligating the hybridized nucleic acids and adapter nucleic acids.

6. The method of claim 4, further comprising:

amplifying the polymerase extended products; and detecting the polymerase extended products present in the subsample.

7. The method of claim 6, wherein the amplifying is selected from the group consisting of: polymerase chain reaction, ligase chain reaction, rolling circle amplification, nucleic acid sequence based amplification, and strand displacement amplification.

8. The method of claim 6, wherein detecting further comprises sequencing at least a portion of the amplified products.

9. The method of claim 4, wherein the detecting further comprises the steps of:

hybridizing a plurality of species of a probe with the polymerase extended products, each of the species of probe capable of hybridizing with the polymerase extended products that have a particular sequence for at least a portion of the composite subsequence; and analyzing which of the species of probe has hybridized with the polymerase extended products, thereby determining the composite subsequence.

10. The method of claim 9, wherein the plurality of species of probes are fixed on a surface such that each of the species of probe is positionally distinguishable from other of the plurality of probes fixed on the surface, to form a plurality of addressable capture molecules.

11. The method of claim 10, wherein the plurality of species of probes comprise a plurality of probe nucleotide sequences, each probe nucleotide sequence having a terminal nucleotide subsequence and a core nucleotide subsequence, wherein the step of hybridizing further comprises:

annealing the plurality of species of probes with the polymerase extended products and with a detector oligomer to form a hybridization structure, wherein the detector oligomer has a sequence that is complementary to a hybridizable portion of at least one of the polymerase extended products to form a plurality of annealed capture molecules; and detecting the annealed capture molecules.

12. The method of claim 11, further comprising, after hybridizing and prior to detecting, ligating nicks in the hybridization structure.

13. The method of claim 10, wherein each of the species of the probes comprises a nucleotide sequence having a terminal nucleotide subsequence and a core nucleotide subsequence, wherein the hybridizing comprises:

annealing a plurality of species of probe with the products to form a hybridization structure;

incubating the hybridization structure with a polymerase and at least one deoxynucleotide triphosphate; and detecting which of the probes is extended.

14. The method of claim 10, wherein each of the species of probe comprises a nucleotide sequence, wherein the nucleotide sequence is a sequence of interest, and wherein the hybridizing comprises:

annealing a plurality of species of probes with the polymerase extended products;

incubating with a polymerase and at least one species of deoxynucleotide triphosphates; and detecting which of the plurality of species of probe is extended.

15. The method of claim 9, wherein the analyzing further comprises:

generating a detectable signal for each of the species of probes hybridized; and quantifying the signal, thereby quantifying the nucleic acids present in the sample.

16. The method of claim 15, wherein the detectable signal generated at each of the species of probes is positionally distinguishable from other of the plurality of probes fixed on the surface.

* * * * *